US012796990B2

(12) United States Patent
Ebrahimi et al.

(10) Patent No.: US 12,796,990 B2
(45) Date of Patent: Nov. 17, 2026

(54) MEDICAL PROBE WITH CONCENTRIC REFERENCE AND SENSE ELECTRODES

(71) Applicant: Biosense Webster (Israel) Ltd., Yokneam (IL)

(72) Inventors: Babak Ebrahimi, Lake Forest, CA (US); Shubhayu Basu, Anaheim, CA (US); Pieter Emmelius Van Niekerk, Rancho Santa Margarita, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 189 days.

(21) Appl. No.: 18/659,258

(22) Filed: May 9, 2024

(65) Prior Publication Data

US 2024/0407696 A1 Dec. 12, 2024

Related U.S. Application Data

(60) Provisional application No. 63/507,154, filed on Jun. 9, 2023.

(51) Int. Cl.

*A61B 5/287* (2021.01)
*A61B 5/00* (2006.01)
*A61B 5/339* (2021.01)

(52) U.S. Cl.

CPC ............ *A61B 5/287* (2021.01); *A61B 5/6859* (2013.01); *A61B 5/339* (2021.01); *A61B 2560/0468* (2013.01); *A61B 2562/046* (2013.01)

(58) Field of Classification Search

CPC ...... A61B 18/1492; A61B 2018/00214; A61B 5/287; A61B 2018/00267;

(Continued)

(56) References Cited

U.S. PATENT DOCUMENTS

| | | | |
|---|---|---|---|
| D265,084 | S | 6/1982 | Goldin |
| 4,699,147 | A | 10/1987 | Chilson et al. |

(Continued)

FOREIGN PATENT DOCUMENTS

| | | | |
|---|---|---|---|
| CN | 102665586 | A | 9/2012 |
| CN | 102892453 | A | 1/2013 |

(Continued)

OTHER PUBLICATIONS

First Office Action and Search Report with English translation dated Sep. 30, 2024, from corresponding Chinese Application No. 202011055244.1.

(Continued)

*Primary Examiner* — Joseph A Stoklosa
*Assistant Examiner* — Brian M Antiskay

(57) ABSTRACT

An electrode combination for an end effector of a catheter may include a reference electrode and a sensing electrode positioned such that the reference electrode is recessed in relation to the sensing electrode so that the reference electrode is inhibited from contacting tissue while the sensing electrode is in contact with tissue. The reference electrode can function to detect far-field electromagnetic noise while the sensing electrode receives electrical signals from tissue and may also receive signals from far-field electromagnetic noise. Electrocardiograms of the electrical signals from tissue can be generated by subtracting, or otherwise compensating for, the far-field noise received by the sensing electrode based on the far-field electromagnetic noise received by the reference electrode. Preferably, the reference electrode and the sensing electrode have the same surface area as each other.

19 Claims, 13 Drawing Sheets

(58) Field of Classification Search
CPC .. A61B 2018/0022; A61B 2018/00351; A61B 2018/1467; A61B 2017/003; A61B 2018/1475; A61B 2018/00285; A61B 2017/00026; A61B 2018/00357; A61B 5/283; A61B 5/6852; A61B 18/082; A61B 17/12136; A61B 2018/1497; A61B 1/00082; A61N 1/362; A61N 1/04; A61M 25/10; A61M 2210/125; A61M 25/0152; A61M 25/00
See application file for complete search history.

(56) References Cited

U.S. PATENT DOCUMENTS 4,940,064 A 7/1990 Desai
5,029,041 A 7/1991 Robinson et al.
D319,045 S 8/1991 Hasegawa et al.
D319,629 S 9/1991 Hasegawa et al.
5,215,103 A 6/1993 Desai
5,255,679 A 10/1993 Imran
5,293,869 A 3/1994 Edwards et al.
5,309,910 A 5/1994 Edwards et al.
5,324,284 A 6/1994 Imran
5,345,936 A 9/1994 Pomeranz et al.
5,365,926 A 11/1994 Desai
5,391,199 A 2/1995 Ben-Haim
5,396,887 A 3/1995 Imran
5,400,783 A 3/1995 Pomeranz et al.
5,411,025 A 5/1995 Webster, Jr.
5,415,166 A 5/1995 Imran
5,443,489 A 8/1995 Ben-Haim
5,456,254 A 10/1995 Pietroski et al.
5,465,717 A 11/1995 Imran et al.
5,476,495 A 12/1995 Kordis et al.
5,499,981 A 3/1996 Kordis
5,515,848 A 5/1996 Corbett, III et al.
5,526,810 A 6/1996 Wang
5,546,940 A 8/1996 Panescu et al.
5,549,108 A 8/1996 Edwards et al.
5,555,883 A 9/1996 Avitall
5,558,073 A 9/1996 Pomeranz et al.
5,558,091 A 9/1996 Acker et al.
5,577,509 A 11/1996 Panescu et al.
5,595,183 A 1/1997 Swanson et al.
5,598,848 A 2/1997 Swanson et al.
5,609,157 A 3/1997 Panescu et al.
5,628,313 A 5/1997 Webster, Jr.
5,630,918 A 5/1997 Takahara et al.
5,681,280 A 10/1997 Rusk et al.
5,702,438 A 12/1997 Avitall
5,722,401 A 3/1998 Pietroski et al.
5,722,403 A 3/1998 McGee et al.
5,725,525 A 3/1998 Kordis
5,730,128 A 3/1998 Pomeranz et al.
5,738,096 A 4/1998 Ben-Haim
5,782,899 A 7/1998 Imran
5,792,149 A 8/1998 Sherts et al.
5,881,727 A 3/1999 Edwards
5,893,847 A 4/1999 Kordis
5,904,680 A 5/1999 Kordis et al.
5,911,739 A 6/1999 Kordis et al.
5,928,228 A 7/1999 Kordis et al.
5,944,022 A 8/1999 Nardella et al.
5,964,757 A 10/1999 Ponzi
5,968,040 A 10/1999 Swanson et al.
5,983,126 A 11/1999 Wittkampf
6,014,579 A 1/2000 Pomeranz et al.
6,014,590 A 1/2000 Whayne et al.
6,071,280 A 6/2000 Edwards et al.
6,071,282 A 6/2000 Fleischman
D429,704 S 8/2000 Kang
6,119,030 A 9/2000 Morency
6,121,554 A 9/2000 Kamikawa
6,123,699 A 9/2000 Webster, Jr.
6,142,993 A 11/2000 Whayne et al.
6,171,277 B1 1/2001 Ponzi
6,172,499 B1 1/2001 Ashe
6,183,435 B1 2/2001 Bumbalough et al.
6,183,463 B1 2/2001 Webster, Jr.
6,198,974 B1 3/2001 Webster, Jr.
D440,209 S 4/2001 Kang
6,210,407 B1 4/2001 Webster
6,216,043 B1 4/2001 Swanson et al.
6,216,044 B1 4/2001 Kordis
D442,150 S 5/2001 Kang
6,239,724 B1 5/2001 Doron et al.
6,245,068 B1 6/2001 Olson et al.
6,267,746 B1 7/2001 Bumbalough
6,332,089 B1 12/2001 Acker et al.
D458,233 S 6/2002 Lee
6,405,067 B1 * 6/2002 Mest .................. A61B 18/1492
606/41
6,415,187 B1 7/2002 Kuzma et al.
6,428,537 B1 8/2002 Swanson et al.
6,445,864 B2 9/2002 Jiang et al.
6,484,118 B1 11/2002 Govari
6,522,932 B1 2/2003 Kuzma et al.
D474,773 S 5/2003 Kondo
6,574,492 B1 6/2003 Ben-Haim et al.
6,584,345 B2 6/2003 Govari
6,590,963 B2 7/2003 Mohammadian et al.
6,600,948 B2 7/2003 Ben-Haim et al.
6,618,612 B1 9/2003 Acker et al.
6,658,302 B1 12/2003 Kuzma et al.
D485,536 S 1/2004 Dang et al.
6,690,963 B2 2/2004 Ben-Haim et al.
6,738,655 B1 5/2004 Sen et al.
6,741,878 B2 5/2004 Fuimaono et al.
6,748,255 B2 6/2004 Fuimaono et al.
6,780,183 B2 8/2004 Jimenez, Jr. et al.
6,788,967 B2 9/2004 Ben-Haim et al.
6,837,886 B2 1/2005 Collins et al.
6,866,662 B2 3/2005 Fuimaono et al.
6,892,091 B1 5/2005 Ben-Haim et al.
6,961,602 B2 11/2005 Fuimaono et al.
6,970,730 B2 11/2005 Fuimaono et al.
6,973,340 B2 12/2005 Fuimaono et al.
6,980,858 B2 12/2005 Fuimaono et al.
7,048,734 B1 5/2006 Fleischman et al.
7,099,712 B2 8/2006 Fuimaono et al.
7,149,563 B2 12/2006 Fuimaono et al.
7,155,270 B2 12/2006 Solis et al.
7,255,695 B2 8/2007 Falwell et al.
7,257,434 B2 8/2007 Fuimaono et al.
7,257,435 B2 8/2007 Plaza
D552,048 S 10/2007 He
7,366,557 B2 4/2008 Bautista
7,399,299 B2 7/2008 Daniel et al.
7,412,274 B2 8/2008 Mejia
7,429,261 B2 9/2008 Kunis et al.
7,511,228 B2 3/2009 Yaung et al.
7,522,950 B2 4/2009 Fuimaono et al.
7,536,218 B2 5/2009 Govari et al.
D600,351 S 9/2009 Phillips et al.
D605,613 S 12/2009 Carter et al.
RE41,334 E 5/2010 Beatty et al.
7,756,567 B2 7/2010 Kuduvalli et al.
7,756,576 B2 7/2010 Levin
7,846,157 B2 12/2010 Kozel
7,848,757 B2 12/2010 Duggi et al.
7,848,787 B2 12/2010 Osadchy
7,869,865 B2 1/2011 Govari et al.
7,930,018 B2 4/2011 Harlev et al.
D637,297 S 5/2011 Erickson et al.
8,007,495 B2 8/2011 McDaniel et al.
8,048,063 B2 11/2011 Aeby et al.
8,103,327 B2 1/2012 Harlev et al.
8,167,845 B2 5/2012 Wang et al.
8,206,404 B2 6/2012 De La Rama et al.
8,224,416 B2 7/2012 De La Rama et al.
8,235,988 B2 8/2012 Davis et al.
8,271,099 B1 9/2012 Swanson
8,273,084 B2 9/2012 Kunis et al.
8,346,339 B2 1/2013 Kordis et al.

(56) References Cited

U.S. PATENT DOCUMENTS

| | | | |
|---|---|---|---|
| 8,391,947 | B2 | 3/2013 | Urman et al. |
| 8,435,232 | B2 | 5/2013 | Aeby et al. |
| 8,447,377 | B2 | 5/2013 | Harlev et al. |
| 8,456,182 | B2 | 6/2013 | Bar-Tal et al. |
| 8,480,669 | B2 | 7/2013 | Pappone et al. |
| 8,498,686 | B2 | 7/2013 | Grunewald |
| 8,517,999 | B2 | 8/2013 | Pappone et al. |
| 8,545,490 | B2 | 10/2013 | Mihajlovic et al. |
| 8,560,086 | B2 | 10/2013 | Just et al. |
| 8,565,851 | B2 | 10/2013 | Lau et al. |
| 8,567,265 | B2 | 10/2013 | Aeby et al. |
| 8,571,626 | B2 | 10/2013 | Lau et al. |
| 8,603,069 | B2 | 12/2013 | Selkee |
| 8,712,550 | B2 | 4/2014 | Grunewald |
| 8,715,279 | B2 | 5/2014 | De La Rama et al. |
| 8,734,440 | B2 | 5/2014 | Wu |
| 8,744,599 | B2 | 6/2014 | Tegg |
| 8,755,861 | B2 | 6/2014 | Harlev et al. |
| 8,764,742 | B2 | 7/2014 | Pappone et al. |
| 8,790,341 | B2 | 7/2014 | Pappone et al. |
| 8,825,130 | B2 | 9/2014 | Just et al. |
| 8,827,910 | B2 | 9/2014 | De La Rama et al. |
| 8,906,011 | B2 | 12/2014 | Gelbart et al. |
| 8,945,120 | B2 | 2/2015 | McDaniel et al. |
| 8,956,353 | B2 | 2/2015 | Govari et al. |
| 8,974,454 | B2 | 3/2015 | De La Rama et al. |
| 8,979,837 | B2 | 3/2015 | De La Rama et al. |
| 8,979,839 | B2 | 3/2015 | De La Rama et al. |
| 9,037,264 | B2 | 5/2015 | Just et al. |
| 9,044,245 | B2 | 6/2015 | Condie et al. |
| 9,131,980 | B2 | 9/2015 | Bloom |
| 9,204,929 | B2 | 12/2015 | Solis |
| 9,277,960 | B2 | 3/2016 | Weinkam et al. |
| 9,314,208 | B1 | 4/2016 | Altmann et al. |
| 9,480,416 | B2 | 11/2016 | Govari et al. |
| 9,480,491 | B1 | 11/2016 | Dostal et al. |
| 9,486,282 | B2 | 11/2016 | Solis |
| 9,545,285 | B2 | 1/2017 | Ghaffari et al. |
| 9,554,718 | B2 | 1/2017 | Bar-Tal et al. |
| 9,561,075 | B2 | 2/2017 | Pappone et al. |
| D782,686 | S | 3/2017 | Werneth et al. |
| 9,585,588 | B2 | 3/2017 | Marecki et al. |
| 9,597,036 | B2 | 3/2017 | Aeby et al. |
| 9,616,199 | B2 | 4/2017 | Wang et al. |
| 9,642,675 | B2 | 5/2017 | Werneth et al. |
| 9,687,297 | B2 | 6/2017 | Just et al. |
| 9,693,733 | B2 | 7/2017 | Altmann et al. |
| 9,724,492 | B2 | 8/2017 | De La Rama et al. |
| 9,782,099 | B2 | 10/2017 | Williams et al. |
| 9,788,895 | B2 | 10/2017 | Solis |
| 9,801,585 | B2 | 10/2017 | Shah et al. |
| 9,801,681 | B2 | 10/2017 | Laske et al. |
| 9,814,618 | B2 | 11/2017 | Nguyen et al. |
| 9,820,664 | B2 | 11/2017 | Hoitink et al. |
| 9,833,161 | B2 | 12/2017 | Govari |
| 9,833,608 | B2 | 12/2017 | Masson |
| 9,848,795 | B2 | 12/2017 | Marecki et al. |
| 9,877,781 | B2 | 1/2018 | Grasse et al. |
| D809,663 | S | 2/2018 | Nachum |
| 9,894,756 | B2 | 2/2018 | Weinkam et al. |
| 9,895,073 | B2 | 2/2018 | Solis |
| 9,907,480 | B2 | 3/2018 | Basu et al. |
| 9,907,609 | B2 | 3/2018 | Cao et al. |
| 9,949,656 | B2 | 4/2018 | Wu et al. |
| 9,962,224 | B2 | 5/2018 | Pappone et al. |
| 9,974,460 | B2 | 5/2018 | Wu et al. |
| 9,986,949 | B2 | 6/2018 | Govari et al. |
| 9,993,160 | B2 | 6/2018 | Salvestro et al. |
| 10,014,607 | B1 | 7/2018 | Govari et al. |
| 10,028,376 | B2 | 7/2018 | Weinkam et al. |
| 10,034,637 | B2 | 7/2018 | Harlev et al. |
| D826,190 | S | 8/2018 | Podubni |
| D826,192 | S | 8/2018 | Podubni |
| 10,039,494 | B2 | 8/2018 | Altmann et al. |
| 10,039,598 | B2 | 8/2018 | De La Rama et al. |
| 10,045,707 | B2 | 8/2018 | Govari |
| 10,078,713 | B2 | 9/2018 | Auerbach et al. |
| D830,319 | S | 10/2018 | Podubni |
| D830,320 | S | 10/2018 | Podubni |
| D832,229 | S | 10/2018 | Podubni |
| 10,111,623 | B2 | 10/2018 | Jung et al. |
| D833,990 | S | 11/2018 | Podubni |
| D834,546 | S | 11/2018 | Podubni |
| 10,130,420 | B2 | 11/2018 | Basu et al. |
| 10,130,422 | B2 | 11/2018 | Ditter |
| 10,136,828 | B2 | 11/2018 | Houben et al. |
| 10,143,394 | B2 | 12/2018 | Solis |
| 10,172,536 | B2 | 1/2019 | Maskara et al. |
| 10,182,762 | B2 | 1/2019 | Just et al. |
| D841,606 | S | 2/2019 | Podubni |
| 10,194,818 | B2 | 2/2019 | Williams et al. |
| 10,201,311 | B2 | 2/2019 | Chou et al. |
| 10,219,860 | B2 | 3/2019 | Harlev et al. |
| 10,219,861 | B2 | 3/2019 | Just et al. |
| 10,220,187 | B2 | 3/2019 | De La Rama et al. |
| 10,231,328 | B2 | 3/2019 | Weinkam et al. |
| 10,238,309 | B2 | 3/2019 | Bar-Tal et al. |
| 10,278,590 | B2 | 5/2019 | Salvestro et al. |
| D851,774 | S | 6/2019 | Werneth et al. |
| 10,314,349 | B2 | 6/2019 | Walsh |
| 10,314,505 | B2 | 6/2019 | Williams et al. |
| 10,314,507 | B2 | 6/2019 | Govari et al. |
| 10,314,648 | B2 | 6/2019 | Ge et al. |
| 10,314,649 | B2 | 6/2019 | Bakos et al. |
| 10,349,855 | B2 | 7/2019 | Zeidan et al. |
| 10,350,003 | B2 | 7/2019 | Weinkam et al. |
| 10,362,991 | B2 | 7/2019 | Tran et al. |
| 10,375,827 | B2 | 8/2019 | Weinkam et al. |
| 10,376,170 | B2 | 8/2019 | Quinn et al. |
| 10,376,221 | B2 | 8/2019 | Iyun et al. |
| 10,398,348 | B2 | 9/2019 | Osadchy et al. |
| 10,403,053 | B2 | 9/2019 | Katz et al. |
| 10,433,903 | B2 | 10/2019 | Pappone et al. |
| 10,441,188 | B2 | 10/2019 | Katz et al. |
| 10,470,682 | B2 | 11/2019 | Deno et al. |
| 10,470,714 | B2 | 11/2019 | Altmann et al. |
| 10,482,198 | B2 | 11/2019 | Auerbach et al. |
| 10,492,729 | B2 | 12/2019 | De La Rama et al. |
| 10,492,857 | B2 | 12/2019 | Guggenberger et al. |
| 10,537,259 | B2 | 1/2020 | Wu et al. |
| 10,542,620 | B2 | 1/2020 | Weinkam et al. |
| 10,575,743 | B2 | 3/2020 | Basu et al. |
| 10,575,745 | B2 | 3/2020 | Solis |
| 10,576,244 | B2 | 3/2020 | De La Rama et al. |
| 10,582,871 | B2 | 3/2020 | Williams et al. |
| 10,582,894 | B2 | 3/2020 | Ben Zrihem et al. |
| 10,596,346 | B2 | 3/2020 | Aeby et al. |
| 10,602,947 | B2 | 3/2020 | Govari et al. |
| 10,617,867 | B2 | 4/2020 | Viswanathan et al. |
| D883,240 | S | 5/2020 | Fathauer |
| 10,660,700 | B2 | 5/2020 | Beeckler et al. |
| 10,660,702 | B2 | 5/2020 | Viswanathan et al. |
| D887,999 | S | 6/2020 | Chen |
| D888,674 | S | 6/2020 | Chen |
| 10,667,753 | B2 | 6/2020 | Werneth et al. |
| 10,674,929 | B2 | 6/2020 | Houben et al. |
| 10,681,805 | B2 | 6/2020 | Weinkam et al. |
| 10,682,181 | B2 | 6/2020 | Cohen et al. |
| 10,687,892 | B2 | 6/2020 | Long et al. |
| 10,702,177 | B2 | 7/2020 | Aujla |
| 10,702,178 | B2 | 7/2020 | Dahlen et al. |
| 10,716,477 | B2 | 7/2020 | Salvestro et al. |
| 10,758,304 | B2 | 9/2020 | Aujla |
| 10,765,371 | B2 | 9/2020 | Hayam et al. |
| 10,772,566 | B2 | 9/2020 | Aujila |
| 10,799,281 | B2 | 10/2020 | Goertzen et al. |
| 10,842,558 | B2 | 11/2020 | Harlev et al. |
| 10,842,561 | B2 | 11/2020 | Viswanathan et al. |
| 10,842,990 | B2 | 11/2020 | De La Rama et al. |
| 10,857,349 | B2 | 12/2020 | De La Rama et al. |
| 10,863,914 | B2 | 12/2020 | Govari et al. |
| 10,881,376 | B2 | 1/2021 | Shemesh et al. |
| 10,898,139 | B2 | 1/2021 | Guta et al. |
| 10,905,329 | B2 | 2/2021 | Bar-Tal et al. |

(56) References Cited

U.S. PATENT DOCUMENTS

| | | | |
|---|---|---|---|
| 10,912,484 | B2 | 2/2021 | Ziv-Ari et al. |
| 10,918,306 | B2 | 2/2021 | Govari et al. |
| 10,939,871 | B2 | 3/2021 | Altmann et al. |
| 10,952,795 | B2 | 3/2021 | Cohen et al. |
| 10,973,426 | B2 | 4/2021 | Williams et al. |
| 10,973,461 | B2 | 4/2021 | Baram et al. |
| 10,987,045 | B2 | 4/2021 | Basu et al. |
| 11,006,902 | B1 | 5/2021 | Bonyak et al. |
| 11,040,208 | B1 | 6/2021 | Govari et al. |
| 11,045,628 | B2 | 6/2021 | Beeckler et al. |
| 11,051,708 | B2 | 7/2021 | Busu et al. |
| 11,051,877 | B2 | 7/2021 | Sliwa et al. |
| 11,109,788 | B2 | 9/2021 | Rottmann et al. |
| 11,116,435 | B2 | 9/2021 | Urman et al. |
| 11,129,574 | B2 | 9/2021 | Cohen et al. |
| 11,160,482 | B2 | 11/2021 | Solis |
| 11,164,371 | B2 | 11/2021 | Yellin et al. |
| D954,666 | S | 6/2022 | Diana et al. |
| D959,675 | S | 8/2022 | Arfaoui et al. |
| 11,642,064 | B2 | 5/2023 | Sterrett et al. |
| D1,014,762 | S | 2/2024 | Harlev et al. |
| D1,016,762 | S | 3/2024 | Horiki et al. |
| 11,918,281 | B2 | 3/2024 | Beeckler et al. |
| D1,029,275 | S | 5/2024 | Huang et al. |
| 12,232,874 | B2 | 2/2025 | Salazar et al. |
| D1,077,231 | S | 5/2025 | Yaacobi et al. |
| D1,077,232 | S | 5/2025 | Yaacobi et al. |
| D1,077,233 | S | 5/2025 | Yaacobi et al. |
| D1,078,050 | S | 6/2025 | Yaacobi et al. |
| D1,078,051 | S | 6/2025 | Blat et al. |
| D1,090,847 | S | 8/2025 | Ebrahimi et al. |
| 2001/0001314 | A1 | 5/2001 | Davison et al. |
| 2002/0131253 | A1 | 9/2002 | Kobayashi |
| 2003/0236455 | A1 | 12/2003 | Swanson et al. |
| 2004/0150388 | A1 | 8/2004 | Cheng et al. |
| 2004/0186469 | A1* | 9/2004 | Woloszko .............. A61B 5/015 606/49 |
| 2004/0199200 | A1 | 10/2004 | Teague et al. |
| 2004/0210121 | A1 | 10/2004 | Fuimaono et al. |
| 2004/0254572 | A1 | 12/2004 | McIntyre et al. |
| 2005/0159741 | A1 | 7/2005 | Paul et al. |
| 2006/0100669 | A1 | 5/2006 | Fuimaono et al. |
| 2006/0167448 | A1 | 7/2006 | Kozel |
| 2006/0253117 | A1 | 11/2006 | Hovda et al. |
| 2007/0093806 | A1 | 4/2007 | Desai et al. |
| 2007/0255273 | A1 | 11/2007 | Fernandez et al. |
| 2007/0276212 | A1 | 11/2007 | Fuimaono et al. |
| 2008/0249463 | A1 | 10/2008 | Pappone et al. |
| 2008/0249522 | A1 | 10/2008 | Pappone et al. |
| 2008/0294158 | A1 | 11/2008 | Pappone et al. |
| 2009/0012517 | A1 | 1/2009 | De La Rama et al. |
| 2009/0198300 | A1 | 8/2009 | Zhang et al. |
| 2009/0250246 | A1 | 10/2009 | Yaung et al. |
| 2010/0076426 | A1 | 3/2010 | De La Rama et al. |
| 2010/0152731 | A1 | 6/2010 | De La Rama et al. |
| 2010/0168647 | A1 | 7/2010 | Tegg et al. |
| 2010/0174177 | A1 | 7/2010 | Wu |
| 2010/0286684 | A1 | 11/2010 | Hata et al. |
| 2011/0118726 | A1 | 5/2011 | De La Rama et al. |
| 2011/0160574 | A1 | 6/2011 | Harlev et al. |
| 2011/0190625 | A1 | 8/2011 | Harlev et al. |
| 2011/0245756 | A1 | 10/2011 | Arora et al. |
| 2011/0288392 | A1 | 11/2011 | De La Rama et al. |
| 2011/0301597 | A1 | 12/2011 | McDaniel et al. |
| 2011/0313417 | A1 | 12/2011 | De La Rama et al. |
| 2012/0010490 | A1 | 1/2012 | Kauphusman et al. |
| 2012/0130217 | A1 | 5/2012 | Kauphusman et al. |
| 2012/0130218 | A1 | 5/2012 | Kauphusman et al. |
| 2012/0172859 | A1 | 7/2012 | Condie et al. |
| 2012/0239031 | A1 | 9/2012 | Pappone et al. |
| 2012/0265130 | A1 | 10/2012 | De La Rama et al. |
| 2012/0271138 | A1 | 10/2012 | Kordis et al. |
| 2012/0296232 | A1 | 11/2012 | Ng |
| 2013/0030426 | A1 | 1/2013 | Gallardo et al. |
| 2013/0085479 | A1 | 4/2013 | De La Rama et al. |
| 2013/0090651 | A1 | 4/2013 | Smith |
| 2013/0172872 | A1 | 7/2013 | Subramaniam et al. |
| 2013/0172883 | A1 | 7/2013 | Lopes et al. |
| 2013/0178850 | A1 | 7/2013 | Lopes et al. |
| 2013/0190587 | A1 | 7/2013 | Lopes et al. |
| 2013/0204340 | A1 | 8/2013 | Conn et al. |
| 2013/0226167 | A1 | 8/2013 | Kaplan et al. |
| 2013/0253504 | A1 | 9/2013 | Fang |
| 2013/0274582 | A1 | 10/2013 | Afonso et al. |
| 2013/0296852 | A1 | 11/2013 | Madjarov et al. |
| 2013/0310825 | A1 | 11/2013 | Pappone et al. |
| 2013/0338467 | A1 | 12/2013 | Grasse et al. |
| 2014/0018788 | A1 | 1/2014 | Engelman et al. |
| 2014/0025063 | A1 | 1/2014 | Kaplan et al. |
| 2014/0025069 | A1 | 1/2014 | Willard et al. |
| 2014/0052118 | A1 | 2/2014 | Laske et al. |
| 2014/0180147 | A1 | 6/2014 | Thakur et al. |
| 2014/0180151 | A1 | 6/2014 | Maskara et al. |
| 2014/0180152 | A1 | 6/2014 | Maskara et al. |
| 2014/0194716 | A1 | 7/2014 | Diep et al. |
| 2014/0200441 | A1 | 7/2014 | Potter et al. |
| 2014/0200639 | A1 | 7/2014 | De La Rama |
| 2014/0207136 | A1 | 7/2014 | De La Rama et al. |
| 2014/0238176 | A1 | 8/2014 | Huszar et al. |
| 2014/0257069 | A1 | 9/2014 | Eliason et al. |
| 2014/0276712 | A1 | 9/2014 | Mallin et al. |
| 2014/0296902 | A1 | 10/2014 | Huszar et al. |
| 2014/0303619 | A1 | 10/2014 | Pappone et al. |
| 2014/0309512 | A1 | 10/2014 | Govari et al. |
| 2014/0316294 | A1 | 10/2014 | Maskara et al. |
| 2014/0316496 | A1 | 10/2014 | Masson et al. |
| 2014/0330269 | A1 | 11/2014 | Pappone et al. |
| 2014/0343546 | A1 | 11/2014 | De La Rama et al. |
| 2015/0011991 | A1 | 1/2015 | Buysman et al. |
| 2015/0025532 | A1 | 1/2015 | Hanson et al. |
| 2015/0034669 | A1 | 2/2015 | Hamilton et al. |
| 2015/0045863 | A1 | 2/2015 | Litscher et al. |
| 2015/0105645 | A1 | 4/2015 | Subramaniam et al. |
| 2015/0105770 | A1 | 4/2015 | Amit |
| 2015/0119878 | A1 | 4/2015 | Heisel et al. |
| 2015/0133919 | A1 | 5/2015 | McDaniel et al. |
| 2015/0208942 | A1 | 7/2015 | Bar-Tal et al. |
| 2015/0209547 | A1 | 7/2015 | De La Rama et al. |
| 2015/0250424 | A1 | 9/2015 | Govari et al. |
| 2015/0270634 | A1 | 9/2015 | Buesseler et al. |
| 2015/0342532 | A1 | 12/2015 | Basu et al. |
| 2015/0342669 | A1 | 12/2015 | Flanagan et al. |
| 2015/0351652 | A1* | 12/2015 | Marecki ............ A61B 18/1492 29/829 |
| 2015/0352257 | A1 | 12/2015 | Early |
| 2015/0366608 | A1 | 12/2015 | Weber et al. |
| 2015/0374252 | A1 | 12/2015 | De La Rama et al. |
| 2016/0073913 | A1 | 3/2016 | Francis et al. |
| 2016/0081746 | A1 | 3/2016 | Solis |
| 2016/0113709 | A1 | 4/2016 | Maor |
| 2016/0143588 | A1 | 5/2016 | Hoitink et al. |
| 2016/0183877 | A1 | 6/2016 | Williams et al. |
| 2016/0213916 | A1 | 7/2016 | De La Rama |
| 2016/0228023 | A1 | 8/2016 | Govari |
| 2016/0228062 | A1 | 8/2016 | Altmann et al. |
| 2016/0242667 | A1 | 8/2016 | Fay et al. |
| 2016/0278853 | A1 | 9/2016 | Ogle et al. |
| 2016/0282461 | A1 | 9/2016 | Reniers |
| 2016/0302858 | A1 | 10/2016 | Bencini |
| 2016/0317093 | A1 | 11/2016 | Berenfeld et al. |
| 2016/0338770 | A1 | 11/2016 | Bar-Tal et al. |
| 2016/0346038 | A1 | 12/2016 | Helgeson et al. |
| 2016/0374753 | A1 | 12/2016 | Wu et al. |
| 2017/0000365 | A1 | 1/2017 | Wu et al. |
| 2017/0007158 | A1 | 1/2017 | Gross et al. |
| 2017/0027638 | A1 | 2/2017 | Solis |
| 2017/0035497 | A1 | 2/2017 | Nagale et al. |
| 2017/0042449 | A1 | 2/2017 | Deno et al. |
| 2017/0049348 | A1 | 2/2017 | Deno et al. |
| 2017/0049349 | A1 | 2/2017 | Sallee et al. |
| 2017/0056105 | A1 | 3/2017 | Steinke et al. |
| 2017/0065227 | A1 | 3/2017 | Marrs et al. |
| 2017/0065341 | A1 | 3/2017 | Pappone et al. |
| 2017/0071494 | A1 | 3/2017 | Solis et al. |

(56) References Cited

U.S. PATENT DOCUMENTS

2017/0071543 A1 3/2017 Basu et al.
2017/0071544 A1 3/2017 Basu et al.
2017/0071665 A1 3/2017 Solis
2017/0095173 A1 4/2017 Bar-Tal et al.
2017/0100187 A1 4/2017 Basu et al.
2017/0105796 A1 4/2017 Pappone et al.
2017/0112404 A1 4/2017 De La Rama et al.
2017/0112405 A1 4/2017 Sterrett et al.
2017/0143227 A1 5/2017 Marecki et al.
2017/0156790 A1 6/2017 Aujla
2017/0165000 A1 6/2017 Basu et al.
2017/0185702 A1 6/2017 Auerbach et al.
2017/0202515 A1 7/2017 Zrihem et al.
2017/0221262 A1 8/2017 Laughner et al.
2017/0224958 A1 8/2017 Cummings et al.
2017/0251978 A1 9/2017 Rodrigo Bort et al.
2017/0265812 A1 9/2017 Williams et al.
2017/0273738 A1 9/2017 Wu
2017/0281031 A1 10/2017 Houben et al.
2017/0281268 A1 10/2017 Tran et al.
2017/0296125 A1 10/2017 Altmann et al.
2017/0296251 A1 10/2017 Wu et al.
2017/0319269 A1 11/2017 Oliverius et al.
2017/0332970 A1 11/2017 Aujla
2017/0347959 A1 12/2017 Guta et al.
2017/0354338 A1 12/2017 Levin et al.
2017/0354339 A1 12/2017 Zeidan et al.
2017/0354364 A1 12/2017 Bar-Tal et al.
2017/0354797 A1 12/2017 De La Rama et al.
2017/0367756 A1 12/2017 Sliwa et al.
2018/0008203 A1 1/2018 Iyun et al.
2018/0028084 A1 2/2018 Williams et al.
2018/0036078 A1 2/2018 Ditter
2018/0042667 A1 2/2018 Pappone et al.
2018/0049803 A1 2/2018 Solis
2018/0050190 A1 2/2018 Masson
2018/0055563 A1 3/2018 Shetake et al.
2018/0056038 A1 3/2018 Aujla
2018/0070845 A1 3/2018 Hoitink et al.
2018/0071017 A1 3/2018 Bar-Tal et al.
2018/0085064 A1 3/2018 Auerbach et al.
2018/0116539 A1 5/2018 Olson et al.
2018/0132749 A1 5/2018 Govari et al.
2018/0137687 A1 5/2018 Katz et al.
2018/0140807 A1 5/2018 Herrera et al.
2018/0160978 A1 6/2018 Cohen et al.
2018/0161577 A1 6/2018 Goedeke et al.
2018/0168511 A1 6/2018 Hall et al.
2018/0185651 A1 7/2018 Astrom et al.
2018/0192958 A1 7/2018 Wu
2018/0193089 A1 7/2018 Wu
2018/0206792 A1 7/2018 Auerbach et al.
2018/0235692 A1 8/2018 Efimov et al.
2018/0249959 A1 9/2018 Osypka
2018/0256109 A1 9/2018 Wu et al.
2018/0279954 A1 10/2018 Hayam et al.
2018/0303361 A1 10/2018 Wu et al.
2018/0303414 A1 10/2018 Toth et al.
2018/0310987 A1 11/2018 Altmann et al.
2018/0311497 A1 11/2018 Viswanathan et al.
2018/0338722 A1 11/2018 Altmann et al.
2018/0344202 A1 12/2018 Bar-Tal et al.
2018/0344251 A1 12/2018 Harlev et al.
2018/0344393 A1 12/2018 Gruba et al.
2018/0360534 A1 12/2018 Teplitsky et al.
2018/0365355 A1 12/2018 Auerbach et al.
2019/0000540 A1 1/2019 Cohen et al.
2019/0008582 A1 1/2019 Govari et al.
2019/0015007 A1 1/2019 Rottmann et al.
2019/0030328 A1 1/2019 Stewart et al.
2019/0053708 A1 2/2019 Gliner
2019/0059766 A1 2/2019 Houben et al.
2019/0069950 A1 3/2019 Viswanathan et al.
2019/0069954 A1 3/2019 Cohen et al.
2019/0099585 A1 4/2019 De La Rama et al.
2019/0110750 A1 4/2019 Dahlen et al.
2019/0117111 A1 4/2019 Osadchy et al.
2019/0117303 A1 4/2019 Claude et al.
2019/0117315 A1 4/2019 Keyes et al.
2019/0125439 A1 5/2019 Rohl et al.
2019/0133552 A1 5/2019 Shemesh et al.
2019/0142293 A1 5/2019 Solis
2019/0164633 A1 5/2019 Ingel et al.
2019/0167137 A1 6/2019 Bar-Tal et al.
2019/0167140 A1 6/2019 Williams et al.
2019/0175056 A1 6/2019 Berkowitz et al.
2019/0188909 A1 6/2019 Yellin et al.
2019/0192221 A1 6/2019 Pappone et al.
2019/0201664 A1 7/2019 Govari
2019/0209089 A1 7/2019 Baram et al.
2019/0216346 A1 7/2019 Ghodrati et al.
2019/0216347 A1 7/2019 Ghodrati et al.
2019/0231421 A1 8/2019 Viswanathan et al.
2019/0231423 A1 8/2019 Weinkam et al.
2019/0239811 A1 8/2019 Just et al.
2019/0246935 A1 8/2019 Govari et al.
2019/0275291 A2 9/2019 de la Rama et al.
2019/0282116 A1 9/2019 Olson
2019/0298442 A1 10/2019 Ogata et al.
2019/0314083 A1 10/2019 Herrera et al.
2019/0328260 A1 10/2019 Zeidan et al.
2019/0343580 A1 11/2019 Nguyen et al.
2019/0350649 A1 11/2019 Sutermeister et al.
2020/0000518 A1 1/2020 Kiernan et al.
2020/0008705 A1 1/2020 Ziv-Ari et al.
2020/0009378 A1 1/2020 Stewart et al.
2020/0015890 A1 1/2020 To et al.
2020/0022653 A1 1/2020 Moisa
2020/0029845 A1 1/2020 Baram et al.
2020/0030024 A1 1/2020 Rao et al.
2020/0038101 A1* 2/2020 Tobey .................. A61B 5/6859
2020/0038103 A1 2/2020 Pappone et al.
2020/0046230 A1 2/2020 McCaffrey et al.
2020/0046421 A1 2/2020 Govari
2020/0046423 A1 2/2020 Viswanathan et al.
2020/0060569 A1 2/2020 Tegg
2020/0077959 A1 3/2020 Altmann et al.
2020/0093539 A1 3/2020 Long et al.
2020/0129089 A1 4/2020 Gliner et al.
2020/0129125 A1 4/2020 Govari et al.
2020/0129128 A1 4/2020 Gliner et al.
2020/0138378 A1 5/2020 De La Rama et al.
2020/0163707 A1 5/2020 Sliwa et al.
2020/0179650 A1 6/2020 Beeckler et al.
2020/0196893 A1 6/2020 McLeod et al.
2020/0196896 A1 6/2020 Solis
2020/0205689 A1 7/2020 Squires et al.
2020/0205690 A1 7/2020 Williams et al.
2020/0205737 A1* 7/2020 Beeckler .............. A61B 5/6853
2020/0205876 A1 7/2020 Govari
2020/0205892 A1 7/2020 Viswanathan et al.
2020/0206456 A1 7/2020 De La Rama et al.
2020/0206498 A1 7/2020 Arora et al.
2020/0253497 A1 8/2020 Sterrett et al.
2020/0289059 A1 9/2020 Montag et al.
2020/0289197 A1 9/2020 Viswanathan et al.
2020/0297234 A1 9/2020 Houben et al.
2020/0297281 A1 9/2020 Basu et al.
2020/0297996 A1 9/2020 De La Rama et al.
2020/0305726 A1 10/2020 Salvestro et al.
2020/0305946 A1 10/2020 Desimone et al.
2020/0330752 A1 10/2020 De La Rama et al.
2020/0345262 A1 11/2020 Selkee et al.
2020/0360080 A1 11/2020 Paamand et al.
2020/0397328 A1 12/2020 Altmann et al.
2020/0398048 A1 12/2020 Krimsky et al.
2021/0015549 A1 1/2021 Haghighi-Mood et al.
2021/0015551 A1 1/2021 Fuentes-Ortega et al.
2021/0022684 A1 1/2021 Govari et al.
2021/0045805 A1 2/2021 Govari et al.
2021/0059549 A1 3/2021 Urman et al.
2021/0059550 A1 3/2021 Urman et al.
2021/0059608 A1 3/2021 Beeckler et al.
2021/0059743 A1 3/2021 Govari

(56) References Cited

U.S. PATENT DOCUMENTS

2021/0059745 A1 3/2021 Highsmith et al.
2021/0059747 A1 3/2021 Krans et al.
2021/0077183 A1* 3/2021 Basu .................... A61B 5/6853
2021/0077184 A1 3/2021 Basu et al.
2021/0082157 A1 3/2021 Rosenberg et al.
2021/0085200 A1 3/2021 Auerbach et al.
2021/0085204 A1 3/2021 Auerbach et al.
2021/0085215 A1 3/2021 Auerbach et al.
2021/0085387 A1 3/2021 Amit et al.
2021/0093292 A1 4/2021 Baram et al.
2021/0093294 A1 4/2021 Shemesh et al.
2021/0093374 A1 4/2021 Govari et al.
2021/0093377 A1 4/2021 Herrera et al.
2021/0100612 A1 4/2021 Baron et al.
2021/0127999 A1 5/2021 Govari et al.
2021/0128010 A1* 5/2021 Govari ................... A61B 5/062
2021/0133516 A1 5/2021 Govari et al.
2021/0145282 A1 5/2021 Bar-Tal et al.
2021/0153932 A1 5/2021 Voth et al.
2021/0161592 A1 6/2021 Altmann et al.
2021/0169421 A1 6/2021 Govari
2021/0169550 A1 6/2021 Govari et al.
2021/0169567 A1 6/2021 Govari et al.
2021/0169568 A1 6/2021 Govari et al.
2021/0177294 A1 6/2021 Gliner et al.
2021/0177356 A1 6/2021 Gliner et al.
2021/0177503 A1 6/2021 Altmann et al.
2021/0178166 A1 6/2021 Govari et al.
2021/0186363 A1 6/2021 Gliner et al.
2021/0186604 A1 6/2021 Altmann et al.
2021/0187241 A1 6/2021 Govari et al.
2021/0196372 A1 7/2021 Altmann et al.
2021/0196394 A1 7/2021 Govari et al.
2021/0212591 A1 7/2021 Govari et al.
2021/0219904 A1 7/2021 Yarnitsky et al.
2021/0278936 A1 9/2021 Katz et al.
2021/0282659 A1 9/2021 Govari et al.
2021/0307815 A1 10/2021 Govari et al.
2021/0308424 A1 10/2021 Beeckler et al.
2021/0338319 A1 11/2021 Govari et al.
2021/0369339 A1 12/2021 Salazar et al.
2022/0054192 A1 2/2022 Beeckler et al.
2022/0054198 A1 2/2022 Tegg et al.
2022/0071695 A1 3/2022 Beeckler et al.
2023/0149069 A1 5/2023 Van Niekerk et al.
2024/0023865 A1 1/2024 Wong et al.
2024/0065755 A1 2/2024 Ebrahimi et al.
2024/0156524 A1 5/2024 Ebrahimi et al.
2024/0197231 A1 6/2024 Rorick
2024/0215893 A1 7/2024 Van Niekerk et al.
2024/0215894 A1 7/2024 Van Niekerk et al.
2025/0032177 A1 1/2025 Henriquez
2025/0213163 A1 7/2025 Ebrahimi et al.

FOREIGN PATENT DOCUMENTS

CN 103220994 A 7/2013
CN 103298392 A 9/2013
CN 103315806 A 9/2013
CN 102892453 B 4/2015
CN 104968261 A 10/2015
CN 102665586 B 3/2016
CN 105534518 A 5/2016
CN 105615994 A 6/2016
CN 103298392 B 8/2016
CN 104968261 B 5/2019
CN 110786926 A 2/2020
CN 111096788 A 5/2020
CN 111248993 A 6/2020
CN 111248996 A 6/2020
EP 0668740 A1 8/1995
EP 0644738 B1 3/2000
EP 0727183 B1 11/2002
EP 0727184 B1 12/2002
EP 2166936 A1 3/2010
EP 2173426 A1 4/2010
EP 2166936 A4 7/2010
EP 2173426 A4 7/2010
EP 2429436 A1 3/2012
EP 2470101 A1 7/2012
EP 2544749 A1 1/2013
EP 2568906 A1 3/2013
EP 2470101 A4 6/2013
EP 2613686 A1 7/2013
EP 2613723 A1 7/2013
EP 2544749 A4 10/2013
EP 2568906 A4 5/2014
EP 2613686 A4 7/2014
EP 2783651 A1 10/2014
EP 2613723 A4 4/2015
EP 2544749 B1 8/2015
EP 2907462 A1 8/2015
EP 2908723 A1 8/2015
EP 2699151 B1 11/2015
EP 2699152 B1 11/2015
EP 1585446 B1 12/2015
EP 2699153 B1 12/2015
EP 2977020 A1 1/2016
EP 2173426 B1 4/2016
EP 2498706 B1 4/2016
EP 3023052 A1 5/2016
EP 2429436 B1 11/2016
EP 3111872 A1 1/2017
EP 3146926 A1 3/2017
EP 3173043 A1 5/2017
EP 2578173 B1 6/2017
EP 3184037 A1 6/2017
EP 2568906 B1 8/2017
EP 3207867 A1 8/2017
EP 2613723 B1 10/2017
EP 2977020 B1 11/2017
EP 3238645 A1 11/2017
EP 3238646 A2 11/2017
EP 2884931 B1 1/2018
EP 3111872 B1 4/2018
EP 3151773 B1 4/2018
EP 3300681 A1 4/2018
EP 2613686 B1 9/2018
EP 2349440 B1 8/2019
EP 3527125 A1 8/2019
EP 3300681 B1 11/2019
EP 3318211 B1 12/2019
EP 3581135 A1 12/2019
EP 2736434 B1 2/2020
EP 2908723 B1 3/2020
EP 3451962 B1 3/2020
EP 2470101 B1 5/2020
EP 3679861 A1 7/2020
EP 3733103 A1 11/2020
EP 3738508 A1 11/2020
EP 3738509 A1 11/2020
EP 3915477 A1 12/2021
EP 3972510 A1 3/2022
JP 2012525933 A 10/2012
JP 2013516218 A 5/2013
JP 2013521892 A 6/2013
JP 2014501557 A 1/2014
JP 2014502195 A 1/2014
JP 2014512227 A 5/2014
JP 5539498 B2 7/2014
JP 2014158957 A 9/2014
JP 5753862 B2 7/2015
JP 5778823 B2 9/2015
JP 2015211874 A 11/2015
JP 2016502912 A 2/2016
JP 2016104129 A 6/2016
JP 6050522 B2 12/2016
JP 6059535 B2 1/2017
JP 6078471 B2 2/2017
JP 2017077479 A 4/2017
JP 2017176879 A 10/2017
JP 2018503435 A 2/2018
JP 6445509 B2 12/2018
JP 2019030685 A 2/2019

(56) References Cited

FOREIGN PATENT DOCUMENTS

| | | | |
|---|---|---|---|
| JP | 2020018857 | A | 2/2020 |
| JP | 2020065933 | A | 4/2020 |
| JP | 2021526401 | A | 10/2021 |
| WO | 9421167 | A1 | 9/1994 |
| WO | 9421169 | A1 | 9/1994 |
| WO | 9625095 | A1 | 8/1996 |
| WO | 9634560 | A1 | 11/1996 |
| WO | 0182814 | A2 | 11/2001 |
| WO | 2004087249 | A2 | 10/2004 |
| WO | 2008124602 | A1 | 10/2008 |
| WO | 2008124619 | A1 | 10/2008 |
| WO | 2009006616 | A1 | 1/2009 |
| WO | 2009023385 | A1 | 2/2009 |
| WO | 2010129661 | A1 | 11/2010 |
| WO | 2011081686 | A1 | 7/2011 |
| WO | 2011112814 | A1 | 9/2011 |
| WO | 2011159861 | A2 | 12/2011 |
| WO | 2011159955 | A1 | 12/2011 |
| WO | 2011159861 | A3 | 2/2012 |
| WO | 2012068505 | A1 | 5/2012 |
| WO | 2012071087 | A1 | 5/2012 |
| WO | 2012100185 | A2 | 7/2012 |
| WO | 2012068505 | A9 | 10/2012 |
| WO | 2013052852 | A1 | 4/2013 |
| WO | 2013162884 | A1 | 10/2013 |
| WO | 2013173917 | A1 | 11/2013 |
| WO | 2013176881 | A1 | 11/2013 |
| WO | 2014113612 | A1 | 7/2014 |
| WO | 2014176205 | A1 | 10/2014 |
| WO | 2015095577 | A1 | 6/2015 |
| WO | 2015130824 | A1 | 9/2015 |
| WO | 2016001015 | A1 | 1/2016 |
| WO | 2016019760 | A1 | 2/2016 |
| WO | 2016044687 | A1 | 3/2016 |
| WO | 2017192712 | A1 | 11/2017 |
| WO | 2018111600 | A1 | 6/2018 |
| WO | 2018191149 | A1 | 10/2018 |
| WO | 2019084442 | A1 | 5/2019 |
| WO | 2019143960 | A1 | 7/2019 |
| WO | 2019177809 | A1 | 9/2019 |
| WO | 2020026217 | A1 | 2/2020 |
| WO | 2020206328 | A1 | 10/2020 |
| WO | 2022032183 | A1 | 2/2022 |
| WO | 240964 | | 9/2025 |

OTHER PUBLICATIONS

Examination Report dated Sep. 6, 2023, from corresponding EP Application No. 20172013.3.

Search Report dated Nov. 29, 2023, from corresponding Japanese Application No. 2020-078996.

Notice of Reasons for Refusal dated Dec. 5, 2023, from corresponding Japanese Application No. 2020-078996.

Written Opinion dated Mar. 5, 2024, from corresponding Japanese Application No. 2020-078996.

Notice of Reasons for Refusal dated May 14, 2024, from corresponding Japanese Application No. 2020-078996.

Written Opinion dated Jul. 23, 2024, from corresponding Japanese Application No. 2020-078996.

Decision to Grant a Patent dated Aug. 6, 2024, from corresponding Japanese Application No. 2020-078996.

Extended European Search Report dated Feb. 27, 2023, from corresponding European Application No. 22194803.7.

Search Report dated Feb. 22, 2024, from corresponding Japanese Application No. 2020-164914.

Notice of Reasons for Refusal dated Feb. 27, 2024, from corresponding Japanese Application No. 2020-164914.

Written Opinion dated May 15, 2024, from corresponding Japanese Application No. 2020-164914.

Decision to Grant a Patent dated May 28, 2024, from corresponding Japanese Application No. 2020-164914.

Extended European Search Report dated Jul. 18, 2023, from corresponding European Application No. 22207377.7.

Extended European Search Report dated Aug. 14, 2023, from corresponding European Application No. 23168941.5.

Extended European Search Report dated Oct. 23, 2023, from corresponding European Application No. 23175980.4.

Extended European Search Report dated Jul. 4, 2024, from corresponding European Application No. 23220720.9.

Extended European Search Report dated Jun. 5, 2024, from corresponding European Application No. 23220734.0.

Broad Offering/High Performance/Cost Saving/Customized/Value Added Flex Cable Assembly, https://www.amphenol-cs.com/product-series/flixible-printed-circuit-assembly.html?page=1, 2025. (Year: 2025).

Basics of Flex Circuit Board Design, https://www.hemeixinpcb.com/company/news/416-basics-of-flex-circuit-design-2.html, May 14, 2022. (Year: 2022).

Extended European Search Report for European Application No. 20172013.3, mailed Sep. 21, 2020, 8 Pages.

Extended European Search Report for European Application No. 20199175.9, mailed Mar. 30, 2021, 07 Pages.

Extended European Search Report for European Application No. 20199230.2, mailed Mar. 18, 2021, 05 Pages.

Extended European Search Report for European Application No. 22194801.1, mailed Dec. 23, 2022, 9 pages.

Extended European Search Report for European Application No. 23163381.9 mailed on May 11, 2023, 5 pages.

International Search Report and Written Opinion issued in International Patent Application No. PCT/IB2022/056738, mailed Oct. 21, 2022, 10 pages.

Extended European Search Reported dated Feb. 27, 2023, from European Patent Application No. 22194803.7.

Exended European Search Report & Opinion dated Aug. 28, 2024, from corresponding European Application No. 24180813.8.

Exam Report dated Jan. 2, 2026, from corresponding European Application No. 24180813.8.

Kurata Kosaku et al: "Feasibility of Concentric Electrodes in Contact Irreversible Electroporation for Superficial Lesion Treatment", IEEE Transactions on Biomedical Engineering, vol. 69, No. 8, Aug. 1, 2022 (Aug. 1, 2022), pp. 2480-2487, XP093184498.

Estrada-Petrocelli Luis et al: "Evaluation of Respiratory Muscle Activity by Means of Concentric Ring Electrodes", IEEE Transactions on Biomedical Engineering, IEEE, USA, vol. 68, No. 3, Jul. 28, 2020 (Jul. 28, 2020), pp. 1005-1014, XP011838437.

* cited by examiner

MEDICAL PROBE WITH CONCENTRIC REFERENCE AND SENSE ELECTRODES

CROSS-REFERENCE TO RELATED APPLICATIONS

This application claims priority to prior filed U.S. Patent Application No. 63/507,154 filed on Jun. 9, 2023, which is hereby incorporated by reference as set forth in full herein.

FIELD

The disclosure relates generally to medical devices, and in particular to electrode catheters configured to measure electrical signals of tissue, particularly cardiac tissue.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many contemporaneous ablation approaches utilize radiofrequency (RF) electrical energy to heat tissue. RF ablation can have certain rare drawbacks due to operator's skill, such as heightened risk of thermal cell injury which can lead to tissue charring, burning, steam pop, phrenic nerve palsy, pulmonary vein stenosis, and esophageal fistula. Cryoablation is an alternative approach to RF ablation that can reduce some thermal risks associated with RF ablation but may present tissue damage due to the very low temperature nature of such devices. Maneuvering cryoablation devices and selectively applying cryoablation is generally more challenging compared to RF ablation; therefore, cryoablation is not viable in certain anatomical geometries which may be reached by electrical ablation devices.

Ablation approaches are being developed which use irreversible electroporation (IRE) to ablate cardiac tissue using nonthermal ablation methods. To achieve IRE, short pulses of high voltage electrical signals are delivered to tissues and the electrical signals generate an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, and 2021/0186604A1, each of which are incorporated herein by reference. U.S. Patent Pub. No. 2021/0169550A1, 2021/0177503A1, and 2021/0186604A1 are attached in the Appendix of priority Patent Application No. 63/507,154.

Regions of cardiac tissue can be mapped by a catheter to identify the abnormal electrical signals. The same or different catheter may be used to perform ablation. Some catheter ablation procedures, especially those with persistent atrial fibrillation, may be performed using electrophysiology (EP) mapping to target areas of aberrant electrical signals. Such EP mapping may include the use of sensing electrodes configured to monitor electrical signals within the cardiovascular system to pinpoint the location of aberrant conductive tissue sites that are responsible for the arrhythmia. Examples of an EP mapping system are described in U.S. Pat. No. 5,738,096, incorporated herein by reference and attached in the Appendix of priority Patent Application No. 63/507,154. Examples of EP mapping catheters are described in U.S. Pat. No. 9,907,480, U.S. Patent Pub. No. 2018/0036078, U.S. Patent Pub. No. 2018/0056038, and U.S. Patent Pub. No. 20210369339, each of which are incorporated herein by reference and attached in the Appendix of priority Patent Application No. 63/507,154.

In addition to using EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO™ 3 system by Biosense Webster, Inc. of Irvine, Calif. Examples of catheters that are configured for use with an IGS system are disclosed in U.S. Pat. No. 9,480,416, incorporated herein by reference and attached in the Appendix of priority Patent Application No. 63/507,154.

SUMMARY

An electrode combination for an end effector of a catheter is presented that includes a reference electrode and a sensing electrode positioned such that the reference electrode is recessed in relation to the sensing electrode so that the reference electrode is inhibited from contacting tissue while the sensing electrode is in contact with tissue. The reference electrode can function to detect far-field electromagnetic noise while the sensing electrode receives electrical signals from tissue and may also receive signals from far-field electromagnetic noise. Electrocardiograms of the electrical signals from tissue can be generated by subtracting, or otherwise compensating for, the far-field noise received by the sensing electrode based on the far-field electromagnetic noise received by the reference electrode. Preferably, the reference electrode and the sensing electrode have the same surface area as each other.

An exemplary end effector for a medical probe can include a first electrode and a second electrode. The first electrode can be disposed on a first side of the end effector. The first electrode can have a first surface exposed to ambient environment and configured to contact tissue. The second electrode can be disposed on the first side of the end effector. The second electrode can be at least partially circumscribed by the first electrode. The second electrode can have a second surface exposed to the ambient environment and inhibited from contacting tissue by virtue of a first vertical gap between the first surface and the second surface.

Another exemplary end effector for a medical probe can include a frame, a first electrode, and a second electrode. The frame member can extend along a longitudinal axis. The first and second electrodes can be disposed generally orthogonal with respect to the longitudinal axis of the frame member so that one of the first and second electrodes is recessed with respect to the other of the first and second electrodes to prevent such recessed electrode from tissue contact.

An exemplary medical probe can include an elongated shaft, an end effector, and a plurality of electrode combinations. The elongated shaft can extend along a longitudinal axis. The end effector can be coupled to a distal end of the elongated shaft. The plurality of electrode combinations can be coupled to the end effector. Each electrode combination of the plurality of electrode combinations can include a respective inner electrode and a respective outer electrode disposed around at least a majority of the respective inner electrode and being vertically offset from the respective inner electrode. Each respective inner electrode and each respective outer electrode can be exposed to ambient environment.

An exemplary method of reducing far-field signals acquired for intracardiac mapping can include the following steps performed in a variety of orders and with interleaving steps as understood by a person skilled in the pertinent art. The method can include locating a first electrode and a second electrode on a generally planar member so that one of the first and second electrodes is recessed with respect to the other of the first and second electrodes. The method can include sensing far-field signals with the recessed one of the first and second electrodes. The method can include sensing cardiac signals with the other of the first and second electrodes. The method can include subtracting far-field signals from the cardiac signals.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements. The figures depict one or more implementations of the inventive devices, by way of example only, not by way of limitation.

DETAILED DESCRIPTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%.

In addition, as used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician.

Alternative apparatus and system features and alternative method steps are presented in example embodiments herein. Each given example embodiment presented herein can be modified to include a feature and/or method step presented with a different example embodiment herein where such feature and/or step is compatible with the given example as understood by a person skilled in the pertinent art as well as where explicitly stated herein. Such modifications and variations are intended to be included within the scope of the claims.

Figure 1:
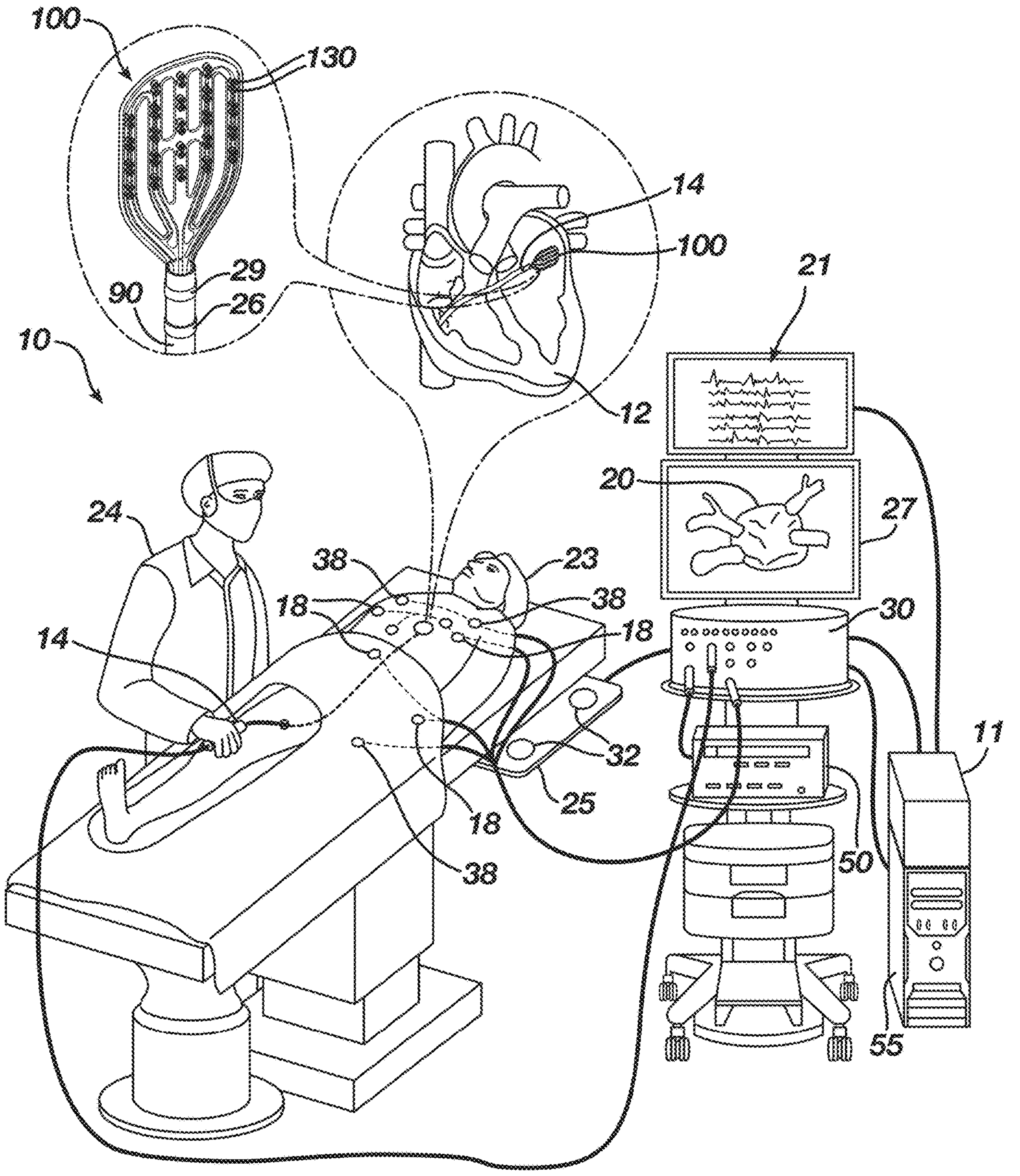
FIG. 1 is an illustration of an example catheter-based electrophysiology mapping and ablation system.

FIG. 1 is an illustration showing an example catheter-based electrophysiology mapping and ablation system 10. The system 10 includes multiple catheters, which are percutaneously inserted by a physician 24 through the patient's vascular system into a chamber or vascular structure of a heart 12. Typically, a delivery sheath catheter is inserted into the left or right atrium near a desired location in the heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating and/or catheters configured for both sensing and ablating. An example catheter 14 that is configured for sensing IEGM is illustrated herein. The physician 24 brings an end effector 100 of the catheter 14 into contact with the heart wall for sensing a target site in the heart 12. For ablation, the physician 24 would similarly bring a distal end of an ablation catheter to a target site for ablating.

The illustrated catheter 14 is an exemplary catheter that includes one and preferably multiple electrodes configured as electrode combinations 130 distributed over a substantially planar surface of the end effector 100 and configured to sense the IEGM signals. Each electrode combination 130 can include a pair of electrodes that are vertically offset from each other so that one electrode is inhibited from contacting tissue while the other electrode is in contact with tissue. The electrode in contact with tissue can function as a sensing electrode and the electrode inhibited from contacting tissue can function as a reference electrode. Electrical signals received by the sensing electrode can primarily include IEGM signals while the electrical signals received by the reference electrode can primarily include far-field signals. The IEGM signals can more accurately be measured by subtracting signals received by the reference electrode from signals received by the sensing electrode, or otherwise reducing the far-field noise in the signals from the sensing electrode based on signals from the reference electrode. IEGM signals measured by the plurality of electrode combinations 130 can be used to determine a spatial relationship of IEGM signals through tissue.

Figure 11A:
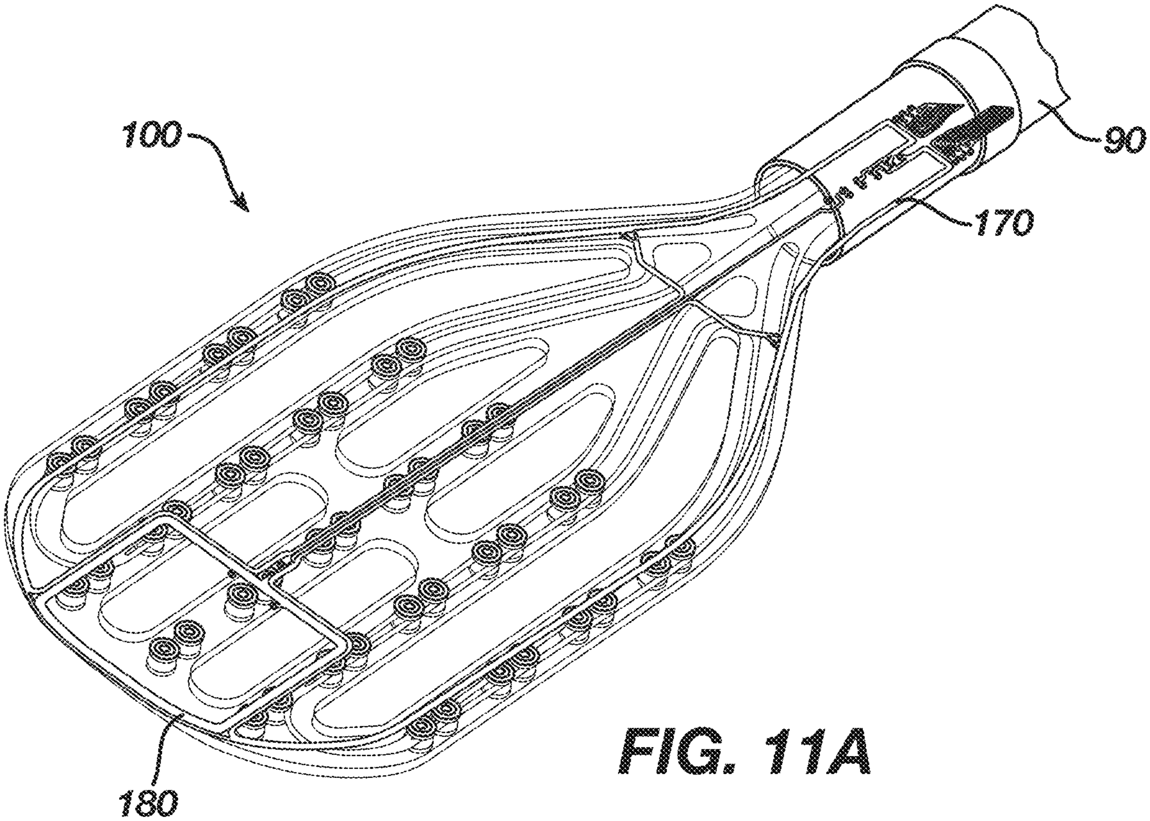
FIGS. 11A and 11B illustrate an exemplary magnetic sensor circuit of the end effector.
Figure 11B:
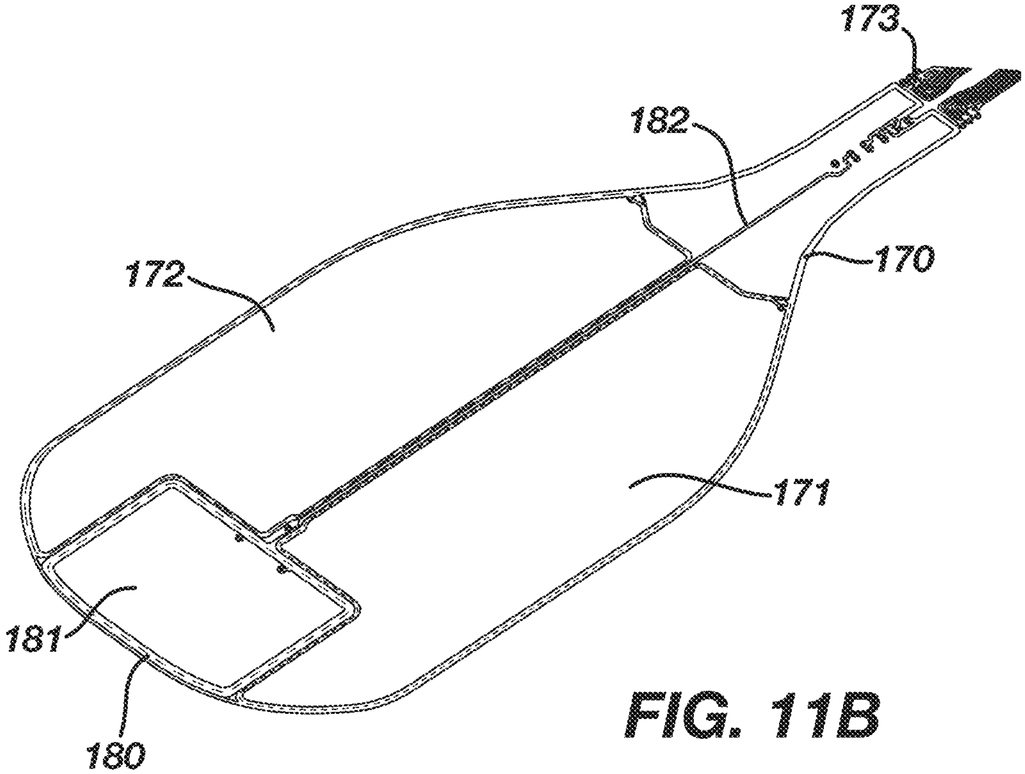

Catheter 14 may additionally include a position sensor 29 coupled to a shaft 90 of the catheter 14 near the end effector 100 for tracking position and orientation of the end effector 100. Optionally and preferably, position sensor 29 is a magnetic based position sensor including three magnetic coils for sensing three-dimensional (3D) position and orientation. The end effector 100 may include additional single axis magnetic sensors 171, 172, 181 such as illustrated in FIGS. 11A and 11B, variations thereof, and alternatives thereto as understood by a person skilled in the pertinent art.

A magnetic based position sensor 29, 171, 172, 181 may be operated together with a location pad 25 including a plurality of magnetic coils 32 configured to generate magnetic fields in a predefined working volume. Real time position of the end effector 100 of the catheter 14 may be tracked based on magnetic fields generated with a location pad 25 and sensed by a magnetic based position sensor 29, 171, 172, 181. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091 incorporated by reference herein.

The system 10 includes one or more electrode patches 38 positioned for skin contact on the patient 23 to establish location reference for location pad 25 as well as impedance-based tracking of electrodes include a shaft electrode 26 and/or electrodes of the end effector electrode combinations 130. For impedance-based tracking, electrical current is directed toward electrodes 26, 130 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182 incorporated by reference herein.

A recorder 11 displays electrograms 21 captured with body surface ECG electrodes 18 and intracardiac electrograms (IEGM) captured with electrode combinations 130 of the catheter 14. The recorder 11 may include pacing capability for pacing the heart rhythm and/or may be electrically connected to a standalone pacer.

The system 10 can include an ablation energy generator 50 that is adapted to conduct ablative energy to one or more of electrodes at a distal tip of a catheter configured for ablating. Energy produced by the ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

A patient interface unit (PIU) 30 is an interface configured to establish electrical communication between catheters, electrophysiological equipment, power supply and a workstation 55 for controlling operation of system 10. Electrophysiological equipment of the system 10 may include for example, multiple catheters, a location pad 25, body surface ECG electrodes 18, electrode patches 38, an ablation energy generator 50, and a recorder 11. Optionally and preferably, the PIU 30 includes processing capability for implementing real-time computations of location of the catheters and for performing ECG calculations.

The workstation 55 includes memory, processor unit with memory or storage with appropriate operating software loaded therein, and user interface capability. The workstation 55 can be configured to provide multiple functions, optionally including (1) modeling the endocardial anatomy in three-dimensions (3D) and rendering the model or an anatomical map 20 for display on a display device 27; (2) displaying on the display device 27 activation sequences (or other data) compiled from recorded electrograms 21 in representative visual indicia or imagery superimposed on the rendered anatomical map 20; (3) displaying real-time location and orientation of multiple catheters within the heart chamber; and (4) displaying on the display device 27 sites of interest such as places where ablation energy has been applied. One commercial product embodying elements of the system 10 is available as the CARTO™ 3 System, available from Biosense Webster, Inc., Irvine, CA 92618.

Figure 2:
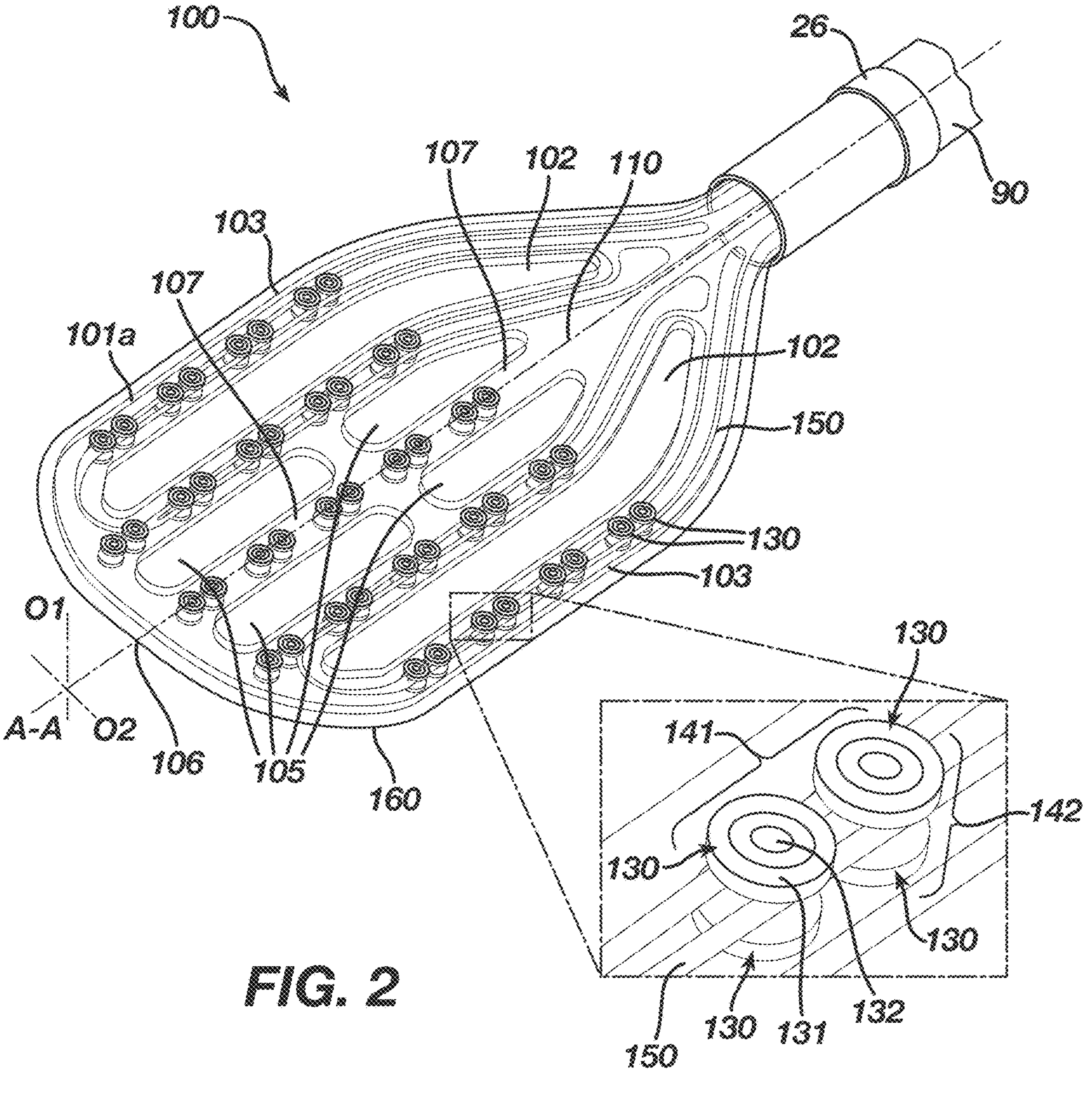
FIG. 2 is an illustration of an exemplary end effector of a catheter.

FIG. 2 is a more detailed illustration of the end effector 100. The shaft 90 of the catheter 14 extends along a longitudinal axis A-A. The end effector 100 is coupled to a distal end of the elongated shaft 90. The end effector 100 is illustrated in a planar configuration such that features of the end effector 100 are orthogonal to a first orthogonal axis O1 that is orthogonal to the longitudinal axis A-A and such that features of the end effector are parallel to a plane including the longitudinal axis A-A and a second orthogonal axis O2 that is orthogonal to the longitudinal axis A-A and the first orthogonal axis O1.

The end effector 100 is configured to collapse to a diameter sized to fit within a sheath catheter for delivery into the heart 12 and configured to expand to the planar configuration (or approximately planar, with some curvature) when pushed distally out of a distal end of the sheath catheter and suspended within bodily fluid. For instance, the end effector 100 can be collapsed by rolling or folding outer portions 103 toward each other to spiral wrap the end effector 100 along the longitudinal axis A-A. The end effector 100 can be held in this collapsed configuration by a delivery sheath catheter when the end effector is delivered through the delivery sheath catheter. The end effector 100 can move from the planar configuration to the collapsed configuration when pulled proximally into a distal end of the sheath catheter.

The end effector 100 is sufficiently flexible such that when pressed against tissue, the end effector is configured to conform to the tissue so that multiple electrodes of the end effector are simultaneously in contact with the tissue. The end effector 100 is sufficiently flexible such that when pressed to a planar surface, the end effector 100 takes on the planar configuration as illustrated in FIG. 2.

Figure 4:
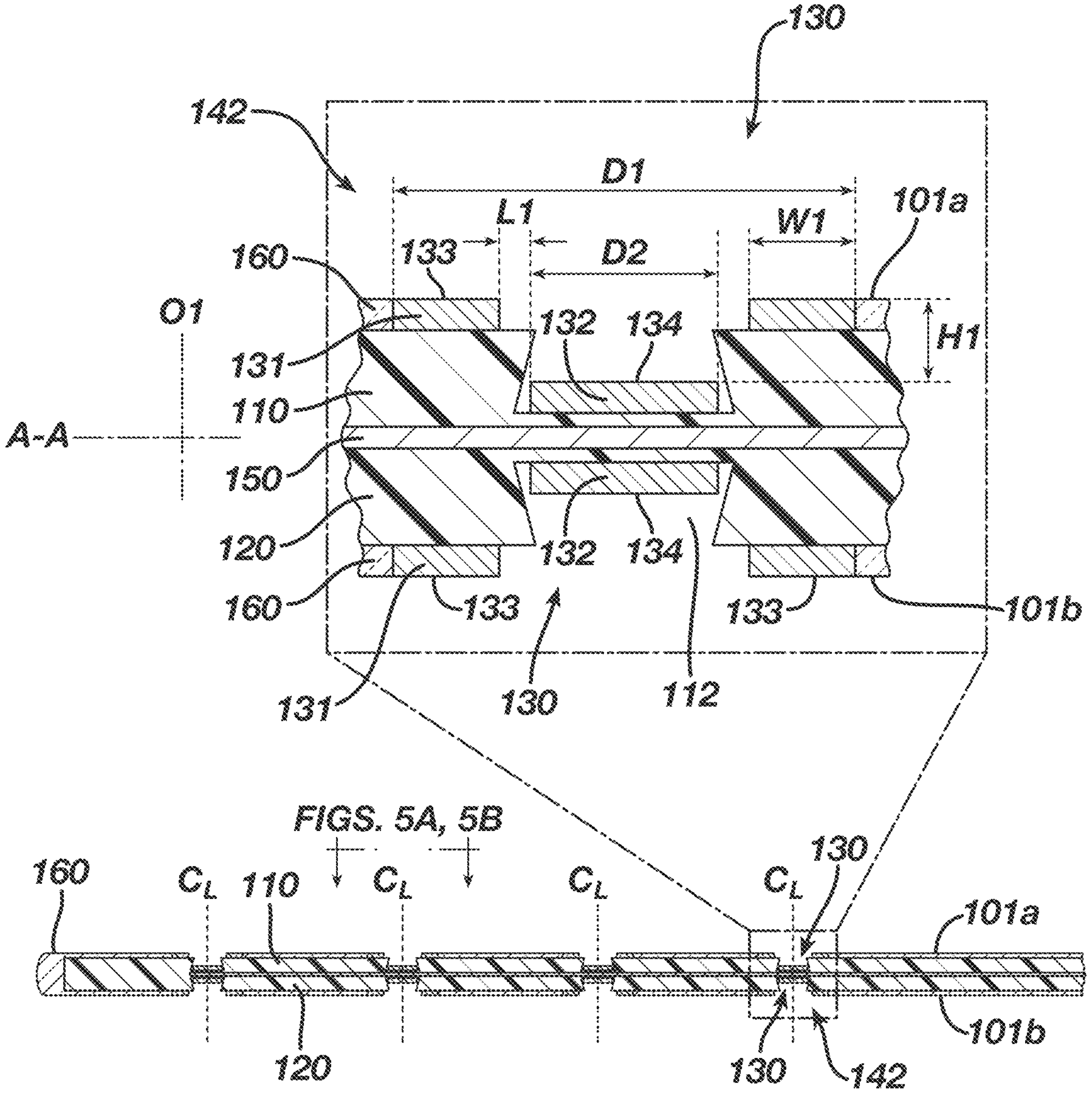
FIG. 4 is a cross-sectional illustration of the exemplary end effector as indicated in FIG. 3A.
Figure 6:
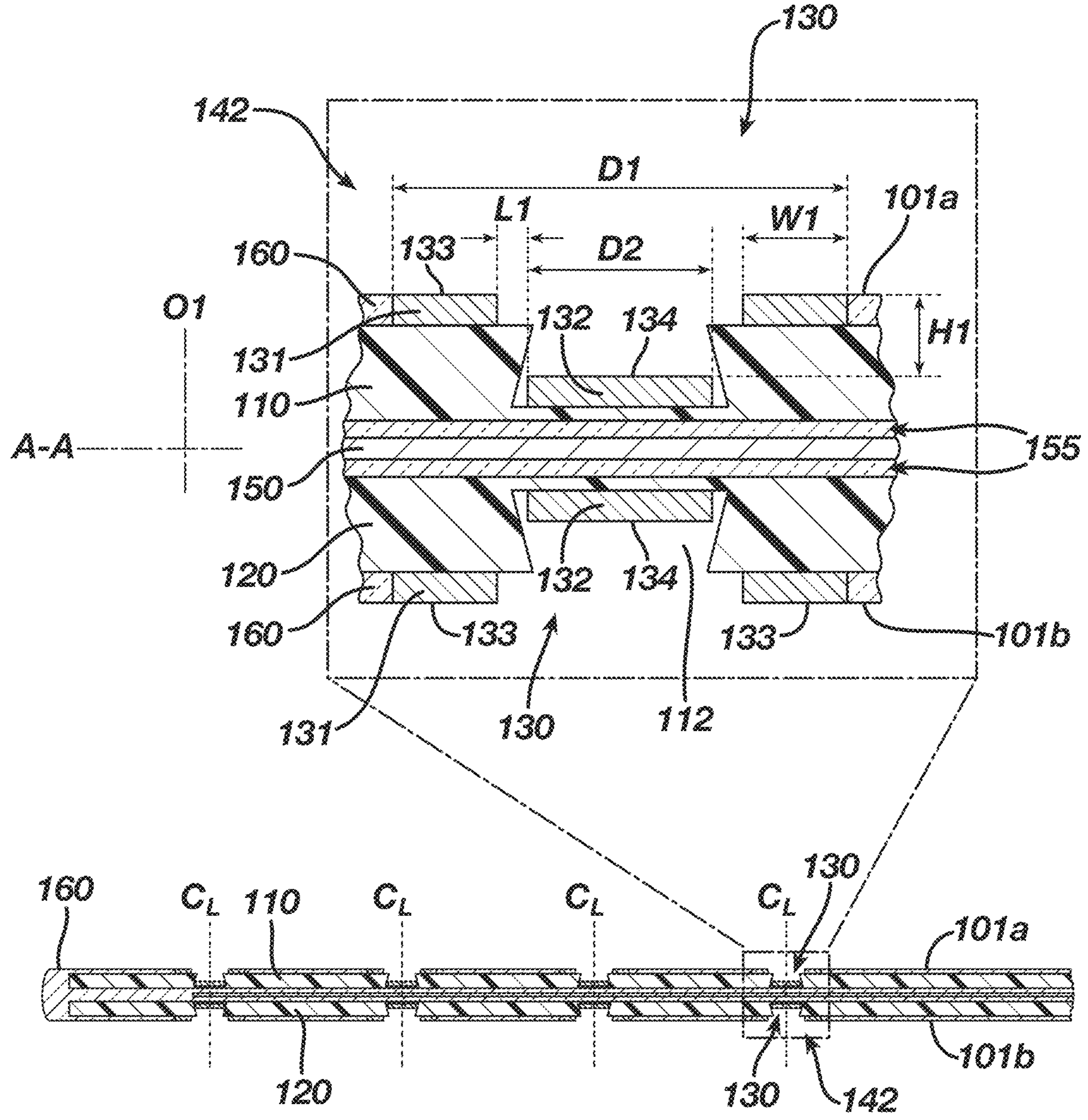
FIG. 6 is a cross-sectional illustration of the exemplary end effector with an additional structural member around a frame.

The end effector can include a frame 150 providing structural support for the end effector 100 and configured to facilitate movement of the end effector 100 into the planar configuration. The end effector can include one or more membranes 110, 120 which extend between struts of the frame 150 (see also FIGS. 4 and 6). The membrane(s) 110, 120 can form a substrate to which electrode combinations 130 can be coupled. The end effector has a first side 101*a* and a second side 101*b* (FIGS. 4 and 6). Each side 101*a*, 101*b* is exposed to ambient environment, and the electrodes of each electrode combination 130 each includes a surface exposed to ambient environment.

The end effector 100 can include openings 102, 105 to provide increased flexibility of the end effector 100. As illustrated, the end effector 100 includes outer openings 102 which extend a majority of a length of the end effector as measured from a distal end of the shaft 90 to a distal end 106 of the end effector. The outer openings 102 separate left and right portions 103 of the end effector from a central portion 107 of the end effector. As illustrated, the end effector 100 includes central openings 105 which extend less than half of the length of the end effector 100. The openings 102, 105 preferably are elongated along the longitudinal axis A-A between columns 138 (FIG. 3A) of electrode combinations 130.

As illustrated, the central portion 107 includes a column of electrode combinations 130 coupled to a portion of the membrane(s) 110, 120 that extends between struts of the frame 150. Therefore, the end effector 100 need not include the frame 150 under every electrode combination 130. At least a portion of the electrode combinations 130 can be coupled to a membrane 110, 120 such that the frame does not extend under the electrode combination 130.

As shown in greater detail in the inset of FIG. 2, each electrode combination includes a first electrode 131 and a second electrode 132. The second electrode 132 is circumscribed by the first electrode 131. As illustrated, the first electrode 131 has a circular annular shape and the second electrode 132 has a circular shape. Alternative geometries are contemplated, for instance, as non-limiting examples: the first electrode 131 can have a square annular shape and the second electrode 132 can have a square shape; the first electrode 131 can have a regular polygon annular shape and the second electrode 132 can have a regular polygon shape; or the first electrode 131 can have an oval annular shape and the second electrode 132 can have an oval shape. Further, the first electrode 131 may be contiguous or may be segmented. Further, the first electrode 131 may have a serpentine annular shape and/or may include interference cuts in an annular shape to provide flexibility of the first electrode 131. Preferably, a majority of the perimeter of the second electrode 132 is circumscribed by the first electrode 131.

The electrode combination 130 includes two electrodes 131, 132 so that one electrode of the electrode combination 130 can function as a sensing electrode and the other electrode in the electrode combination 130 can function as a reference electrode. The reference electrode can function to detect far-field electromagnetic noise while the sensing electrode receives electrical signals from tissue and may also receive signals from far-field electromagnetic noise. Electrocardiograms of the electrical signals from tissue can be generated by subtracting, or otherwise compensating for, the far-field noise received by the sensing electrode based on the far-field electromagnetic noise received by the reference electrode.

The electrodes 131, 132 in the electrode combination can be offset vertically such that the reference electrode is inhibited from contacting tissue while the sensing electrode is in contact with tissue by virtue of a vertical gap between exposed surfaces of the two electrodes 131, 132. The reference electrode therefore is in contact with fluids (e.g. blood) while the sensing electrode is in contact with tissue. In some examples, the first electrode 131 (outer electrode) is configured as the sensing electrode and the second electrode 132 (inner electrode) is configured as the reference electrode. Alternatively, the end effector 100 can be modified so that the second electrode 132 is raised vertically in relation to the first electrode 131 so that the first electrode 131 functions as the reference electrode and the second electrode 132 functions as the reference electrode. In some examples, the end effector 100 can include two types of electrode combinations: a first type electrode combination 130 in which the first electrode 131 (outer electrode) is configured as a sensing electrode and the second electrode 132 (inner electrode) is configured as a reference electrode; and a second type electrode combination 130 in which the first electrode 131 (outer electrode) is configured as a reference electrode and the second electrode 132 (inner electrode) is configured as a sensing electrode.

The electrode combinations 130 can be spaced apart from each other forming longitudinal pairs 141. Each longitudinal pair 141 can include two electrode combinations 130 that are both on the same side 101*a*, 101*b* of the end effector 100. The longitudinal pair 141 therefore includes two sensing electrodes, one from each electrode combination 130 in the longitudinal pair. The sensing electrodes can be configured to measure electrocardiogram signals as a bipolar pair. For instance, the first electrodes 131 from each electrode combination 130 can be configured as sensing electrodes, and the first electrodes 131 can be configured to measure electrocardiogram signals as a bipolar pair. As stated above, the second electrode 132 in an electrode combination 130 can, as an alternative, be configured as a sensing electrode, and an end effector may include both a first type and a second type of electrode combinations 130. Therefore, the bipolar pair functionality of the longitudinal pair 141 may be between two outer electrodes 131, two inner electrodes 132, or an outer electrode 131 and inner electrode 132, depending on the type(s) of electrode combinations in the longitudinal pair 141.

The electrode combinations 130 can be positioned to form orthogonal pairs 142. Each orthogonal pair 142 can include a first electrode combination 130 on the first side 101*a* of the end effector 100 and a second electrode combination 130 on the second side 101*b* of the end effector 100 opposite the first electrode combination 130. The orthogonal pairs 142 can be used to further compensate for far-field noise. While a sensing electrode in one electrode combination is in contact with tissue, the reference electrode in that same electrode combination is detecting far-field noise immediately adjacent tissue while the electrodes of the opposite electrode combination are detecting far-field noise in blood in an orientation that is facing away from tissue. Therefore, in addition to using signals from the respective reference electrode to compensate for far-field noise in the signal detected by the sensing electrode, the signals detected from electrodes in the opposite electrode combination can also be used to compensate for far-field noise.

The end effector 100 can further include a flexible polymer layer 160 as an outer encapsulation, discussed in greater detail in relation to FIG. 4.

Figure 3A:
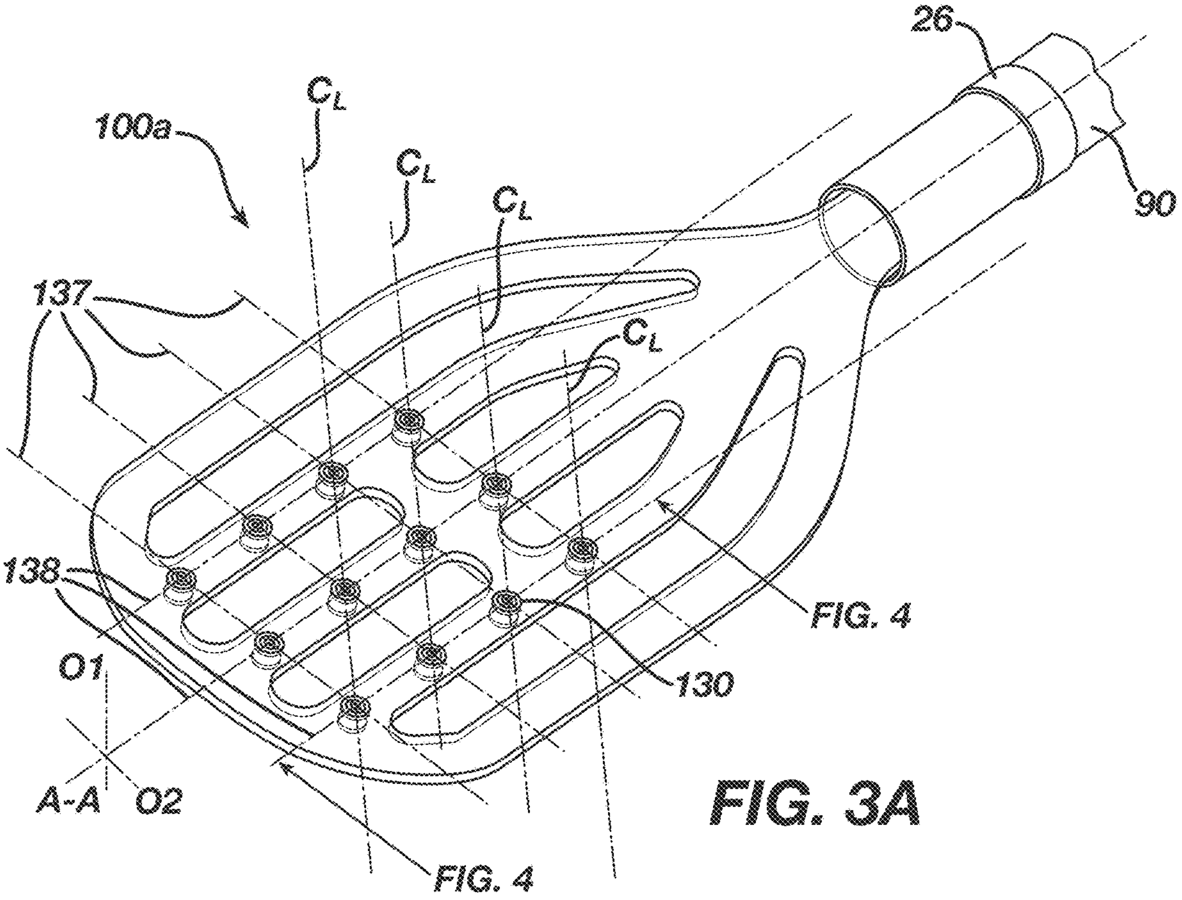
FIG. 3A is an illustration of the exemplary end effector with an alternative electrode configuration.

FIG. 3A is an illustration of the exemplary end effector 100 with an alternative electrode configuration. The electrode combinations 130 are spaced apart in a regular grid having rows 137 of electrode combinations 130 and columns 138 of electrode combinations. The rows 137 are aligned along the second orthogonal axis. The columns 138 are aligned along the longitudinal axis A-A. The alternative electrode configuration does not include longitudinal pairs 141. The alternative electrode configuration does include orthogonal pairs 142. The orthogonal pairs 142 are aligned vertically along a centerline CL along the first orthogonal axis O1, and therefore orthogonal to the end effector 100 in the planar configuration. The electrode pairs 130 and alignment are discussed in greater detail in relation to FIG. 4.

Figure 3B:
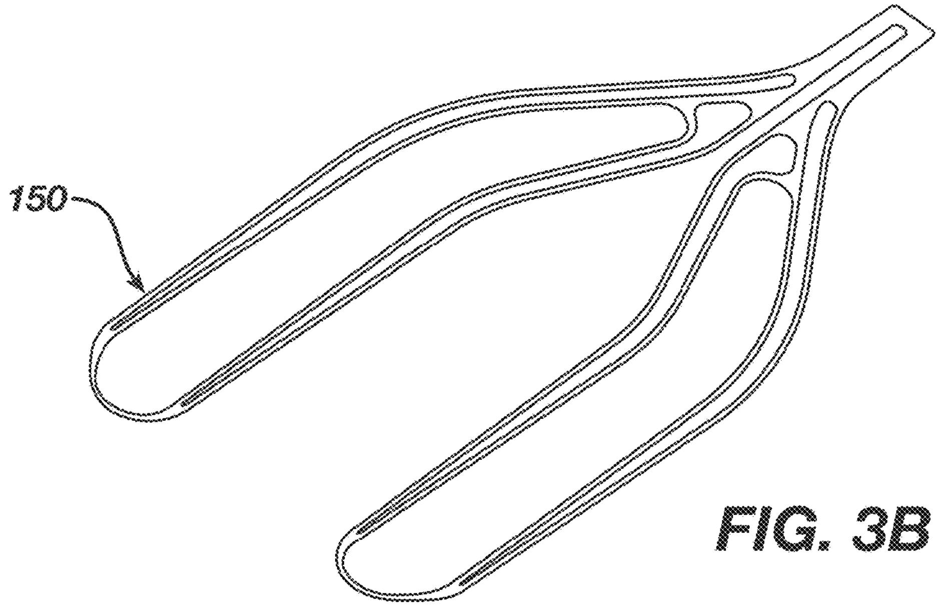
FIG. 3B is an illustration of a frame of the exemplary end effector.

FIG. 3B is an illustration of a frame 150 of the exemplary end effector. The end effector can include a frame 150 providing structural support for the end effector and configured to facilitate movement of the end effector 100 into the planar configuration. The frame 150 can include a resilient material and can include a memory shape material such as nitinol. The frame 150 can be symmetric about the longitudinal axis A-A as illustrated, but need not be symmetrical about the longitudinal axis A-A.

FIG. 4 is a cross-sectional illustration of the exemplary end effector 100 as indicated in FIG. 3A. Top surfaces 133, 134 of the first electrode 131 and the second electrode 132 are each exposed to ambient environment. The top surfaces 133, 134 of the two electrodes 131, 132 are separated by a vertical gap H1. The top surface of the second electrode 132 is inhibited from contacting tissue while the top surface of the first electrode 131 is in contact with tissue by virtue of the vertical gap H1. When the first electrode 131 is pressed into tissue, tissue may have some elasticity to curve downward around edges of the first electrode 131, extending downward beyond the top surface 133 of the first electrode 131. The vertical gap H1 is great enough to inhibit the tissue from extending down to make contact with the top surface 134 of the second electrode 132 during typical use cases of the catheter 14.

Figure 5A:
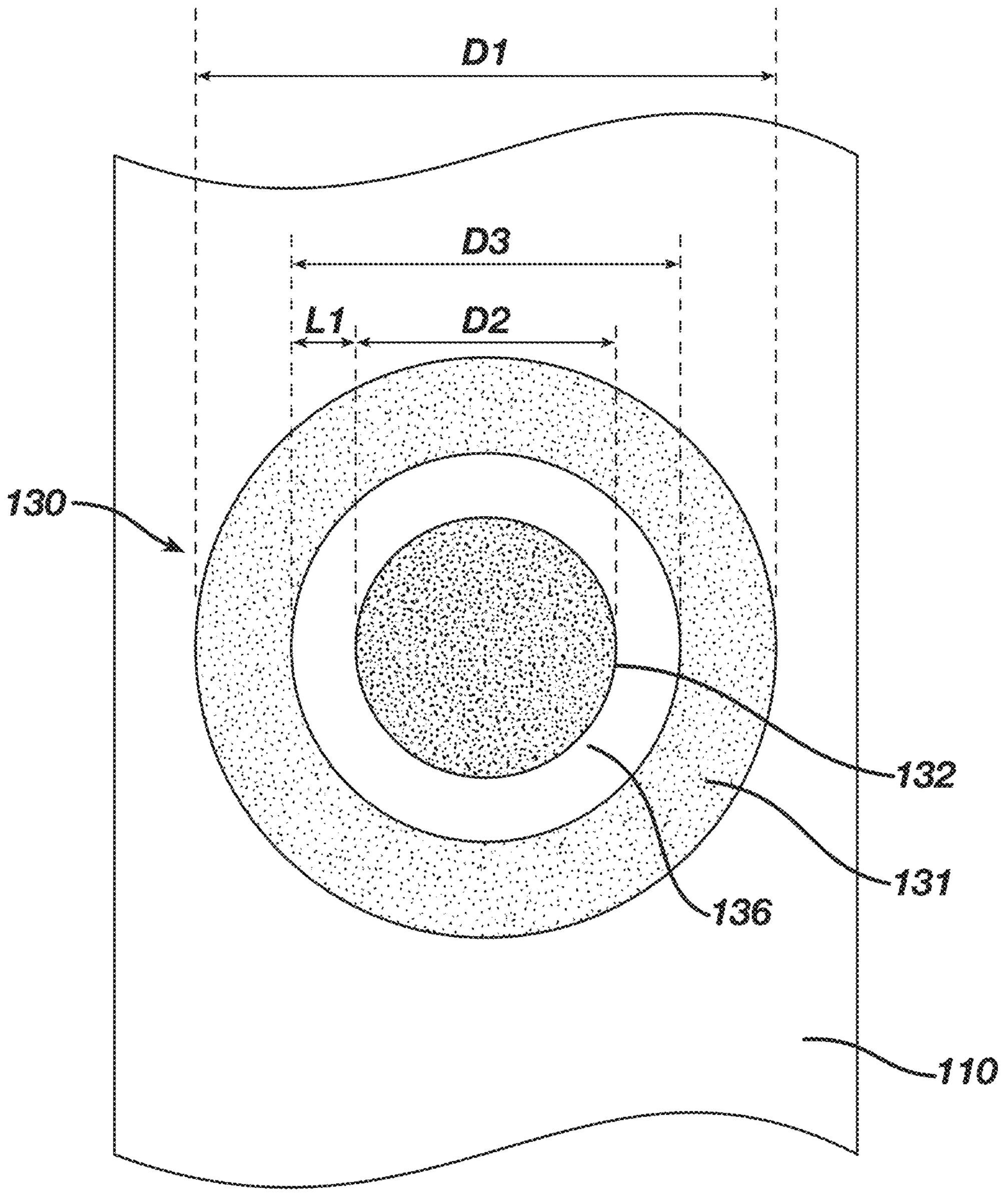
FIGS. 5A, 5B, and 5C are top-down views of an electrode combination of the end effector as indicated in FIG. 4.
Figure 5B:
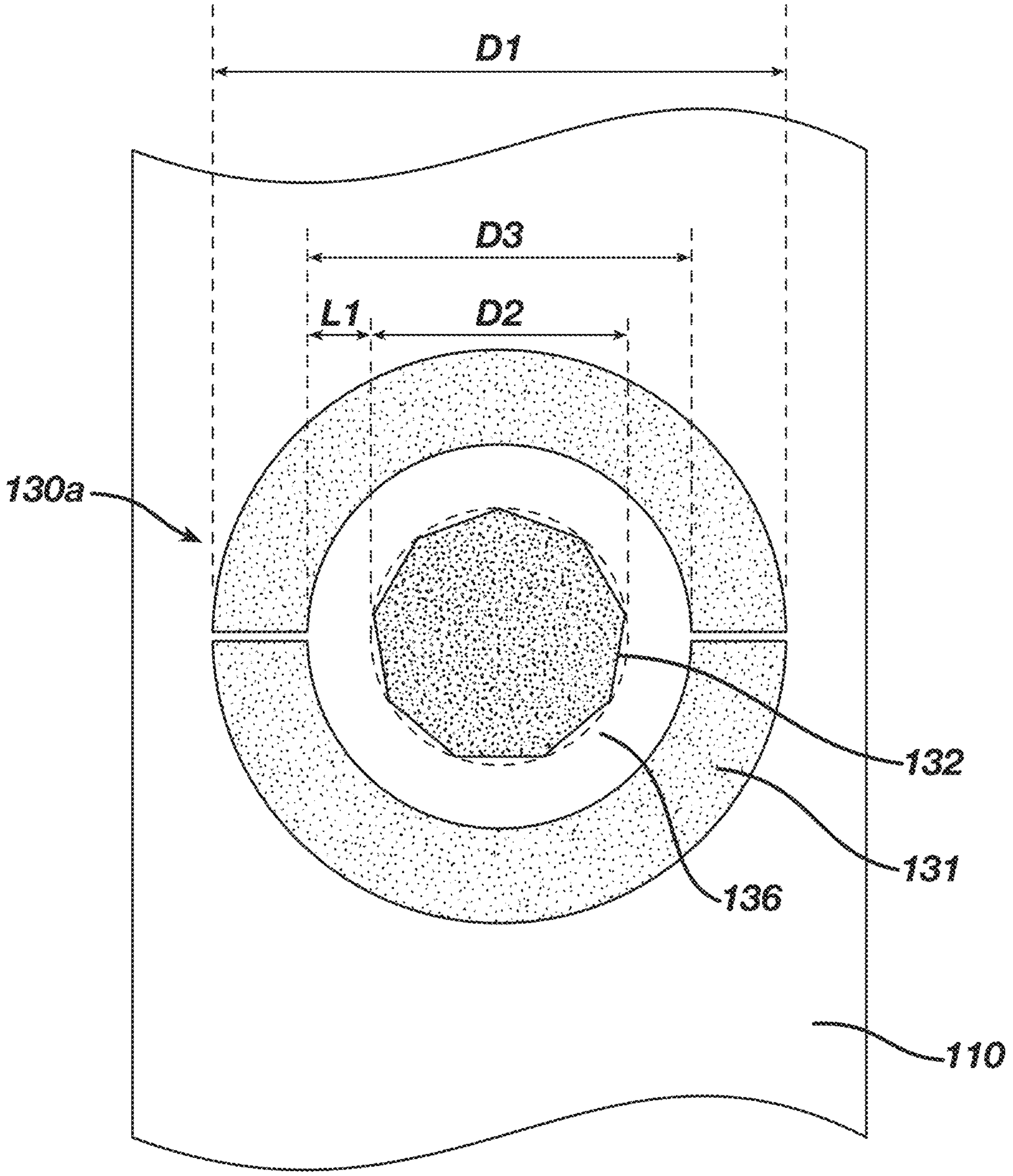
Figure 5C:
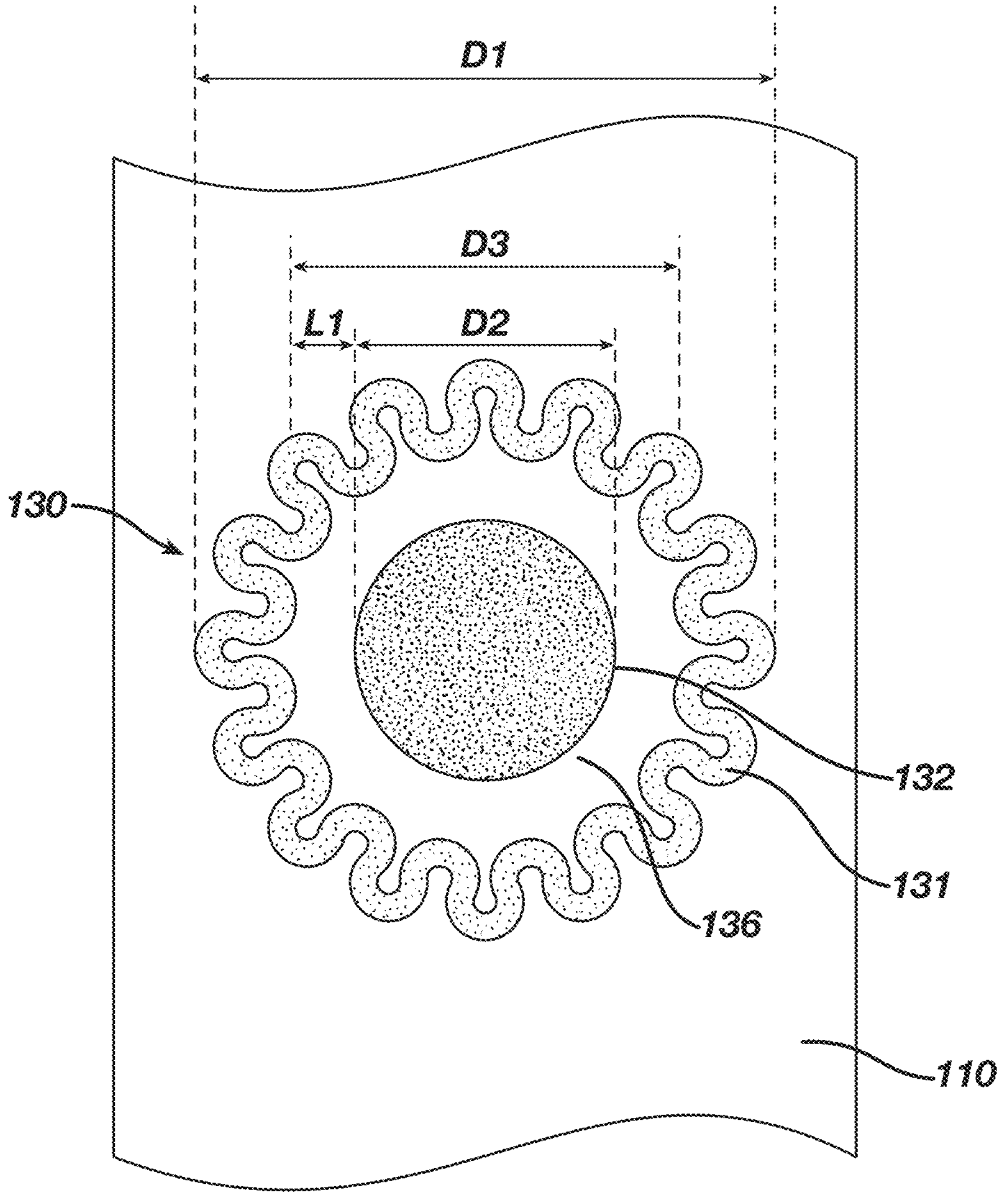

FIGS. 5A, 5B, and 5C are top-down views of various possible configurations of the electrode combination 130 of the end effector 100 as indicated in FIG. 4. FIG. 5A illustrates the first electrode 131 having an uninterrupted circular annular shape and the second electrode 132 having a continuous circular shape. FIG. 5B illustrates the first electrode 131 having an interrupted circular annular shape and the second electrode 132 having a polygon shape. FIG. 5C illustrates the first electrode 131 having a serpentine continuous circular shape which can increase flexibility of the first electrode 131. These are examples of several possible electrode shapes.

Dimensions such as an inner diameter D3 of the first electrode 131 may affect the minimum vertical gap H1 required to inhibit tissue from making contact with the top surface 134 of the second electrode 132 during typical use cases of the catheter 14. The amount of force the end effector 100 is configured to apply to tissue may also affect the minimum vertical gap H1 required to inhibit tissue from making contact with the top surface 134 of the second electrode 132 during typical use cases of the catheter 14. The amount of force the end effector 100 is configured to apply to tissue may be primarily affected by flexibility of the end effector 100, which may be primarily affected by flexibility of the frame 150. Flexibility of tissue may also affect the minimum vertical gap H1 required to inhibit tissue from making contact with the top surface 134 of the second electrode 132.

Referring collectively to FIGS. 4, 5A, 5B, and 5C a first surface area of the top surface 133 of the first electrode 131 can be calculated based its dimensions (i.e. outer diameter D1, inner diameter D3, annular width W1, and shape). A second surface area of the top surface 134 of the second electrode 132 can be calculated by its dimensions (i.e. outer diameter D2, and shape). Preferably, the first surface area is approximately equal to the second surface area.

The first surface 133 and the second surface 134 can be spaced laterally from each other by a lateral gap area 136 having a gap length L1. The surface area of the lateral gap area 136 can be calculated as by taking the area of a circle or polygon having a diameter equal to the inner diameter D3 of the first surface 133 and subtracting the area of a circle or polygon having a diameter equal to the outer diameter D2 of the second surface 134. Thus, the surface area of the lateral gap area 136 can be calculated as a planar surface area parallel to the first surface 133, parallel to the second surface 134, and laterally between the first and second surfaces. The surface area of the lateral gap area 136 can be equal to or less than the first surface area of the first surface 133 and equal to or less than the second surface area of the second surface 134. The annular width W1 of the first surface 133 can be equal to or greater than the gap length L1. The outer diameter D2 of the second surface 134 can be equal to or greater than the gap length L1. Preferably, the lateral gap area 136 is has a surface area that is about 0.83 times, to about equal to, the second surface area and/or the first surface area.

In one example, the first electrode 131 has an outer diameter D1 measuring from about 0.5 mm to about 0.67 mm, and the second electrode 132 has an outer diameter D2 measuring about 0.44 mm. In one example, the first and second surface areas each measure about 0.15 $mm^2$.

Preferably, the first surface 133 and the second surface 134 are each planar, extend along the longitudinal axis A-A, and face orthogonal to the longitudinal axis A-A as illustrated.

Referring to FIG. 4, the end effector 100 can include the frame 150, a first membrane 110 on the first side 101*a* of the end effector 100, a second membrane 120 on the second side 101*b* of the end effector 100, and an encapsulation 160 over the first and second membranes 110, 120.

The membranes 110, 120 can each include a recess or depression 112 into which the reference electrode is positioned to create the vertical gap H1 between the top surfaces of the sensing electrode and the reference electrode. The depression 112 is illustrated as a circular depression, but may have alternative shapes according to an alternative shape of the electrodes 131, 132 of the electrode combination 130.

The inner electrode 132 is disposed in the depression 112 and the outer electrode 131 circumscribes the depression 112 as illustrated. Alternatively, the depression 112 may be configured to circumscribe the inner electrode 132, and the outer electrode 131 may be positioned in the depression so that the outer electrode 131 is inhibited from contacting tissue by virtue of a vertical gap H1 and configured to function as the reference electrode while the inner electrode 132 is configured as the sensing electrode (FIG. 8B). The depression may include an overhang as illustrated and disclosed in greater detail in relation to FIG. 8A.

The membranes 110, 120 can include a flex circuit, also referred to in the art as a flexible printed circuit board (PCB), or flex PCB. The membranes 110 can include layers of flexible dielectric film, such as a polymer film, and one or more patterned conductive (e.g. metallic) layers. The membranes 110, 120, therefore may include multiple layers. In some examples, the polymer film can be made primarily of polyimide. In other examples, the flex circuits can be made of any of biocompatible polyimides, glass-reinforced epoxy laminate materials, copper, or graphene, alone or in combination. For the sake of simplifying the illustration, layers of the membranes 110, 120 are not illustrated. The depression 112, therefore may be constructed by forming an opening in one or more upper layers of the flex circuit and/or other polymer film of a given membrane 110, 120. As illustrated, the electrodes 131, 132 can include conductive disks that are electrically and mechanically coupled to the flex circuit. Additionally, or alternatively, electrodes 131, 132 can include an exposed portion of a conductive layer so that the conductive layer includes an exposed top surface 133, 134.

As illustrated, electrode combinations 130 in each orthogonal pair 142 are aligned vertically along a centerline CL along the first orthogonal axis O1, wherein the centerline CL passes through a central point of each electrode combination 130 of the orthogonal pair 142. The inner electrodes of the electrode combinations 130 of orthogonal pair 142 can be aligned vertically with each other, and the outer electrodes of the electrode combinations 130 of the orthogonal pair 142 can be aligned vertically with each other. It is noted that the scope of the invention does not require each electrode combination 130 to have their centerline CL coincident with each other. That is, the center line CL of the electrode combination 130 on the first membrane 110 can be offset from its counterpart centerline CL for the electrode combination 130 on the second membrane 120. An orthogonal pair 142 includes two electrode combinations that at least partially overlap when the centerlines CL are offset from each other.

The end effector 100 can further include a flexible polymer layer 160 encapsulating the membranes 110, 120 and frame 150. The flexible polymer layer 160 can include openings so that the electrodes 131, 132 are exposed to ambient environment. In some examples, flexible polymer layer 160 can include an outer surface having thinner portions surrounding the electrode combinations 130 and thicker portions at an approximate midpoint between electrode combinations 130. This can improve the ability of the sense electrodes of the electrode combinations 130 to lie flatter against the target anatomy. Alternatively, flexible polymer layer 160 can include an outer surface having thicker portions surrounding the electrode combinations 130. In some examples the frame 150 can be embedded in the flexible polymer layer 160 separate from the flexible circuit of the membranes 110, 120. This can increase the stiffness of the end effector 100. In some examples, the flexible polymer layer 160 can include biocompatible silicone. In other examples, the flexible polymer layer 160 can include biocompatible flexible polymers, thermoelastic polymer materials, and dielectric materials. The flexible polymer layer 160 can optionally be colored to facilitate laser cutting.

FIG. 6 is a cross-sectional illustration of the exemplary end effector with an additional structural member 155 around the frame 150. The structural member 155 can be disposed between the flex circuits of the membranes 110, 120 and around the frame 150 to provide a planar surface to mount the flex circuits. The structural member 155 can be selected from a group of materials such as polymer, metallic, semi-metallic, rigid, elastic or super elastic material and combinations hereof.

The end effector 100 can further be modified to include various geometries of the frame 150, various electrode arrangements, various geometries of the membranes 110, 120, and other compatible features and variations.

Figure 7:
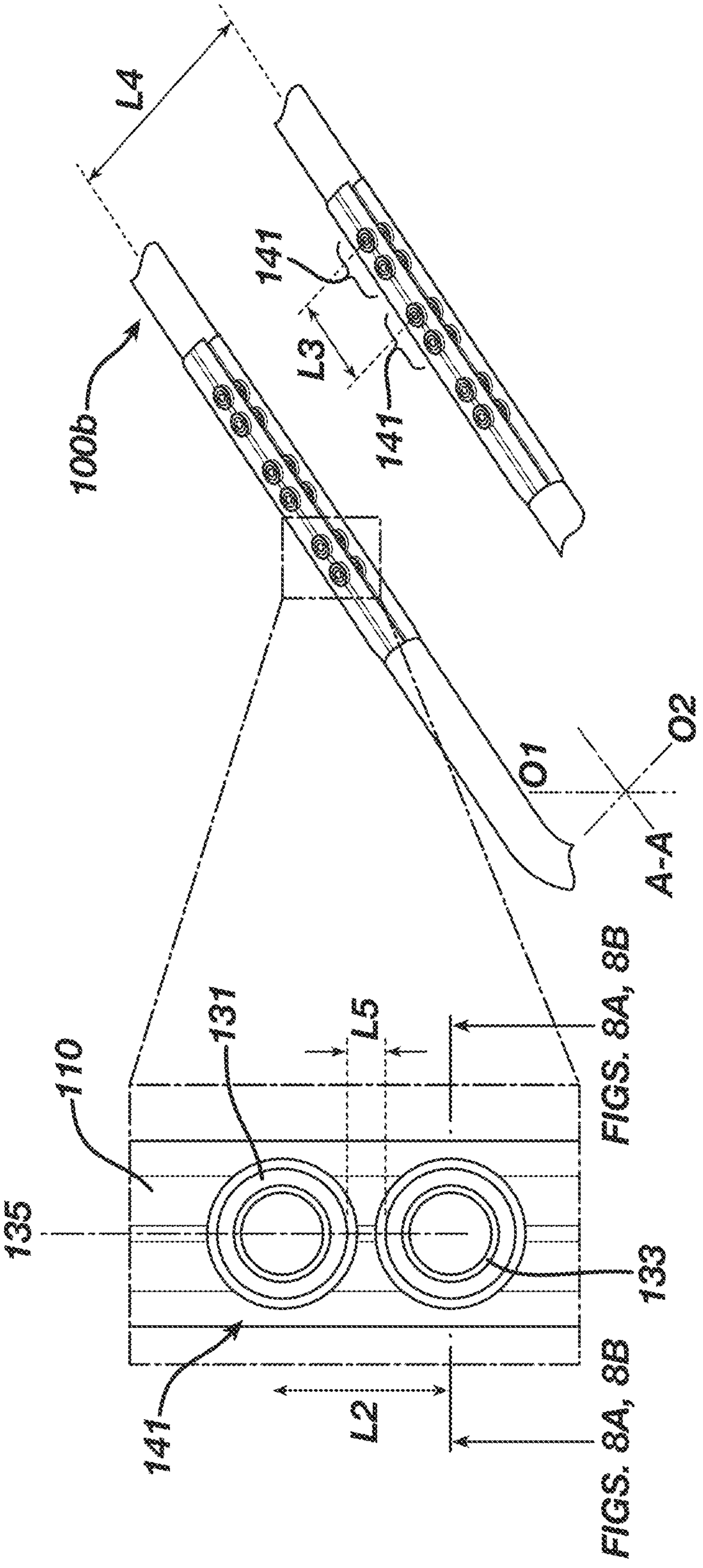
FIG. 7 is an illustration of the exemplary end effector with an alternative electrode support structure.

FIG. 7 is an illustration of the exemplary end effector 100 with an alternative electrode support structure. The end effector 100 includes spines 190 that provide structural support for the electrode combinations 130. The spines 190 may include a flexible tubular housing and a support frame extending through the flexible tubular housing. The support frame can provide structural support to the spines to cause the spines to expand to a predetermined configuration upon exiting a sheath catheter similar to the structural functionality of frame 150 (FIG. 3B). The tubular housing can have various configurations. Wiring and other components can be disposed within a lumen of the tubular housing. For instance, the tubular housing and components disposed therein can be configured similar to the spines disclosed in U.S. Patent Pub. No. 2021/0369339, incorporated by reference herein and attached in the Appendix of priority Patent Application No. 63/507,154.

The electrode combinations 130 can be mounted to a membrane 110 that is affixed to a spine 190, for instance a polymeric tubular housing of the spine 190. The membrane 110 can include a flex circuit configured as disclosed in greater detail elsewhere herein.

Each membrane 110 can include longitudinal pairs 141 of electrode combinations 130*a*, 130*b*. Each longitudinal pair 141 can be configured as a bipolar pair. Therefore, the end effector 100 can include a plurality of bipolar pairs 141, each of the bipolar pairs comprising a first electrode combination 130*a* and a second electrode combination 130*b*, the first electrode combination 130*a* can include a first and second electrode configured as a sensing electrode and a reference electrode. The second electrode combination 130*b* can include a third electrode and a fourth electrode configured as a sensing electrode and a reference electrode. The reference electrode can be vertically depressed in relation to the sensing electrode in the first electrode combination 130*a* and the second electrode combination 130*b*.

As shown in the inset of FIG. 7, a longitudinal pair 141 can include a first (outer) electrode with a first surface 133*a*, a second (inner) electrode with a second surface 134*a*, a third (outer) electrode with a third surface 133*b*, and a fourth (inner) electrode with a fourth surface 134*b*. The four electrodes are coupled to the same side of the end effector 100. The first electrode, and thereby the first surface 133*a* can be longitudinally aligned with the third electrode, and thereby the third surface 133*b*. The second electrode, and thereby the second surface 134*a* can be longitudinally aligned with the fourth electrode, and thereby the fourth surface 134*b*. The longitudinal pairs 141 illustrated in FIG. 2 can likewise be configured similarly as described in relation to FIG. 7.

The first surface 133*a* and the third surface 133*b* are each exposed to ambient environment and configured to contact tissue. The second surface 134*a* is circumscribed by the first surface 133*a*. The fourth surface 134*b* is circumscribed by the third surface 133*b*. The second surface 134*a* and the fourth surface 134*b* are each exposed to the ambient environment.

The longitudinal pair 141 can include two electrode combinations, each with a sensing electrode and a reference electrode. The sensing electrodes can be longitudinally aligned. The reference electrodes can also be longitudinally aligned.

In one example, the second surface 134*a* is inhibited from contacting tissue by virtue of a vertical gap H1 (FIG. 8A) between the second surface 134*a* and the first surface 133*a*. The fourth surface 134*b* is inhibited from contacting tissue by virtue of a vertical gap H1 (FIG. 8A) between the third surface 133*b* and the fourth surface 134*b*. The vertical gaps are measured along the first orthogonal axis O1. The third surface 133*b* is preferably coplanar with the first surface 133*a*. The first electrode and the third electrode may be configured to measure electrocardiogram signals as a bipolar pair.

In another example, the first surface 133*a* is inhibited from contacting tissue by virtue of a vertical gap H2 (FIG. 8B) between the second surface 134*a* and the first surface 133*a*. The third surface 133*b* is inhibited from contacting tissue by virtue of a vertical gap H2 (FIG. 8B) between the third surface 133*b* and the fourth surface 134*b*. The vertical gaps are measured along the first orthogonal axis O1. The second surface 134*a* is preferably coplanar with the fourth surface 134*b*. The second electrode and the fourth electrode may be configured to measure electrocardiogram signals as a bipolar pair.

In another example, the longitudinal pair 141 includes two types of electrode combinations (FIGS. 8A and 8B), wherein the inner electrode is recessed in one of the electrode combinations and the outer electrode is recessed in the other electrode combination.

The electrode combinations 130 of the longitudinal pair 141 can be spaced apart from each other by a predetermined spacing. The third surface 133*b* is spaced apart from the first surface 133*a* by a lateral gap L5 (as illustrated in FIG. 7) which is the shortest distance, measured edge-to-edge from the first surface 133*a* to the third surface 133*b*. The electrode combinations 130 can be spaced apart from each other by a longitudinal spacing L2 measured between central points of each electrode combination 130, i.e. from a central point of the second surface 134*a* to a central point of the fourth surface 134*b*. Longitudinal pairs 141 can be spaced apart from each other by a longitudinal spacing L3 as measured from a central point or center of mass of surface areas of the electrodes of each longitudinal pair 141. For instance, the longitudinal spacing L3 between longitudinal pairs 141 can be measured from a central point between electrode combinations 130 of a first longitudinal pair 141*a* to a central point between electrode combinations 130 of a second longitudinal pair 141*b* as illustrated.

The electrodes can be arranged in columns along spines of the end effector 100*b*. The spines are separated by a column spacing L4 so that the columns of electrodes are separated by the column spacing L4.

Figure 8A:
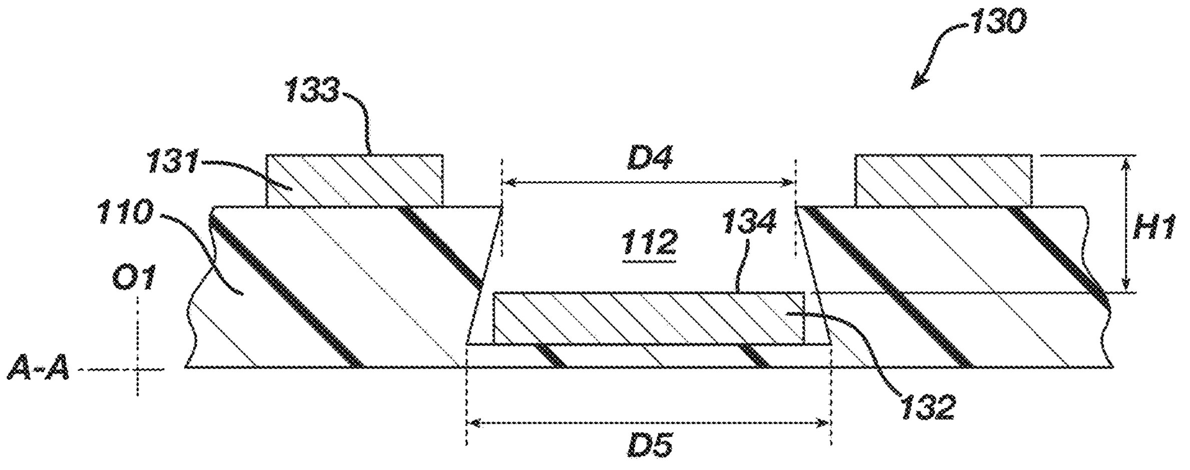
FIGS. 8A, 8B, and 8C are illustrations of alternative embodiments of a cross-section of an electrode combination as indicated in FIG. 7.
Figure 8B:
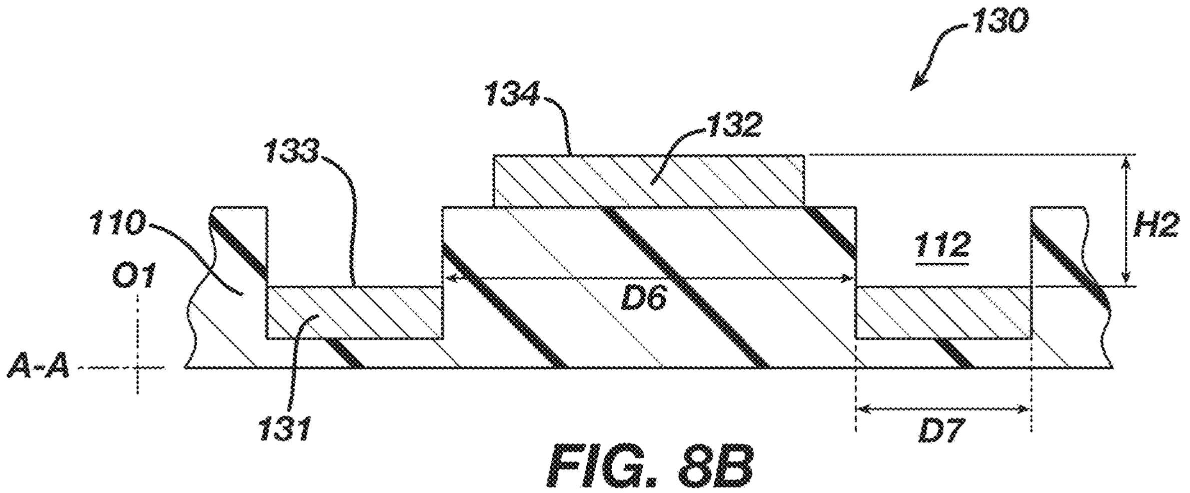
Figure 8C:
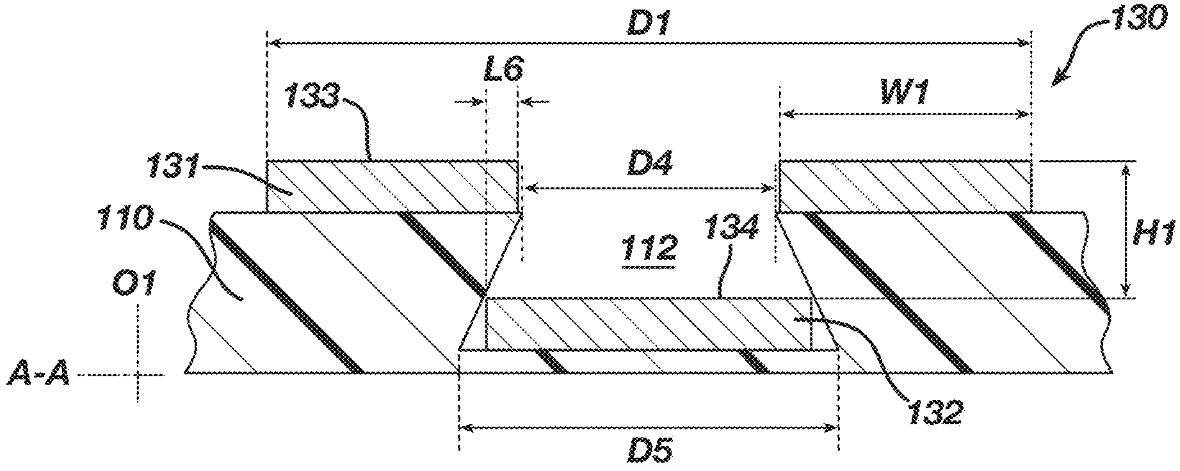

FIGS. 8A, 8B, and 8C are illustrations of a cross-section of an electrode combination 130. FIG. 8A is an illustration of a first type of electrode combination 130 in which the second electrode 132 is recessed in relation to the first electrode 131. FIG. 8B is an illustration of a second type of electrode combination 130 in which the first electrode 131 is recessed in relation to the second electrode 132. FIG. 8C is an illustration of a first type of electrode combination 130 in which the second electrode 132 is recessed in relation to the first electrode 131 and the first electrode 131 overhangs the second electrode 132 by an overhang length L6.

As illustrated in FIG. 8A, the membrane 110 can be shaped such that the recessed electrode is positioned in a depression 112 that has an overhang, so that a top perimeter 114 of the depression 112 overhangs a bottom perimeter 115 of the depression. When the geometry of the electrode combination 130 is circular, as illustrated, the bottom perimeter 115 of the depression 112 can have a diameter D5 that is greater than a diameter D5 of the top perimeter 114. As such, a bottom surface area of the depression 112 can be greater than a top surface area of the depression 112, wherein the bottom surface area is defined as a surface area within the bottom perimeter 115 and the top surface area is defined as a surface area with the top perimeter 114. Likewise, the membranes 110, 120 illustrated in FIGS. 4 and 6 may include such an overhang in the depression 112. Likewise the electrode combination 130 as illustrated in FIG. 8B can be modified to include an overhang over the first electrode 131. Further, reference electrodes having an alternative geometry may be positioned within an alternatively shaped recess having an overhang. The overhang can inhibit the reference electrode from contacting tissue when the sensing electrode is in contact with tissue.

Alternatively, as illustrated in FIG. 8B, the membrane 110 need not include an overhang over the recessed electrode. In this example, the recess 112 has a substantially uniform width D7 along the first orthogonal axis O1, and the second electrode 132 is positioned on a mesa having a substantially uniform width D6 along the first orthogonal axis O1.

Alternatively, as illustrated in FIG. 8C, the membrane 110 can be shaped such that the recessed electrode is positioned in a depression 112 that has an overhang, so that a top perimeter 114 of the depression 112 overhangs a bottom perimeter 115 of the depression. The overhang can be such that the first electrode 131 overlaps the second electrode 132 by an overlap length L6. This construction may allow the width W1 of the first electrode to me made greater without increasing the diameter D1 of the first electrode 131, thereby increasing the contact surface area of the first electrode 131. The effective surface area 132 may remain approximately the same compared to an electrode combination design similar to as illustrated in FIG. 8A, with the second electrode 132 having the same surface area of top surface 133 in both FIGS. 8A and 8C.

Figure 9:
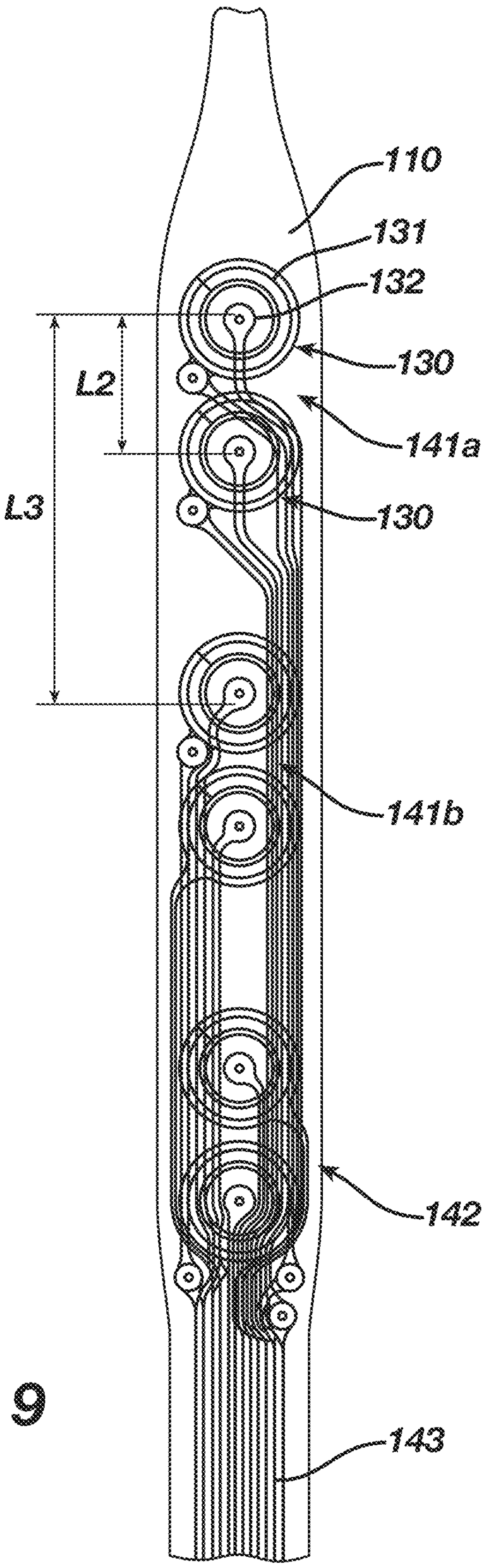
FIG. 9 is an illustration of an exemplary flex circuit layout which can be used to support electrode combinations of the exemplary end effector.

FIG. 9 is an illustration of an exemplary membrane 110 having a flex circuit layout which can be used to support electrode combinations 130 of the exemplary end effector 100. As discussed in greater detail herein, the flex circuit can include multiple layers and can include one or more patterned conductive layers 143. FIG. 9 illustrates patterns of conductive layers of the flex circuit. A longitudinal gap L2 between electrode combinations 130 of a first longitudinal pair 142*a* is illustrated. A longitudinal gap L3 between the first longitudinal pair 141*a* and a second longitudinal pair 141*b* is illustrated.

Figure 10:
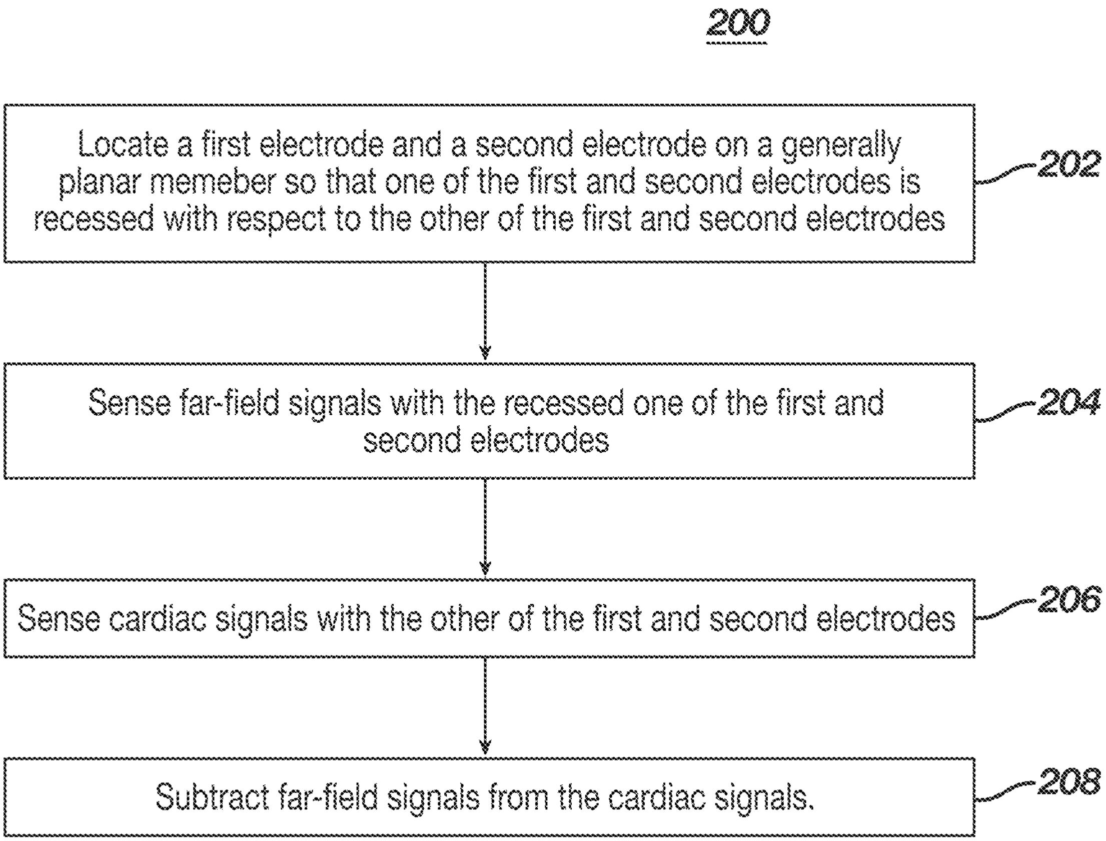
FIG. 10 is a flow diagram of method steps that can be used to detect cardiac signals.

FIG. 10 is a flow diagram 200 of method steps that can be used to detect cardiac signals. At block 202, a first electrode and a second electrode can be located on a generally planar member so that one of the first and second electrodes is recessed with respect to the other of the first and second electrodes. The first and second electrode can be configured in an electrode combination 130. At block 204, far-field signals can be sensed with the recessed one of the first and second electrode. At block 206, cardiac signals can be sensed with the other of the first and second electrodes. At block 208, far-field signals can be subtracted from the cardiac signals.

FIGS. 11A and 11B illustrate an exemplary magnetic sensor circuit of the end effector 100. The end effector 100 can include a plurality of inductive coils or loops 171, 172, 181 each having a respective axis orthogonal to the end effector 100 in the planar configuration. As illustrated, the end effector 100 includes a first inductive loop 181, a second inductive loop 171, and a third inductive loop 173. The first inductive loop 181 is disposed approximate a distal end of the end effector 100. A majority of the second inductive loop 171 and a majority of the third inductive loop 172 are disposed in a proximal direction in relation to the first inductive loop 181. The second inductive loop 171 and the third inductive loop 172 can be elongated along the longitudinal axis and positioned as mirror images of each other about the longitudinal axis. The first inductive loop 181 can be rectangular. The loops 171, 172, 181 can be coplanar with each other. The flexible polymer layer 160 can have layers removed inside the coils 171, 172, 181 in order to make the end effector 100 more flexible while maintaining geometrical integrity and sensing ability of the coils 171, 172, 181. The loops 171, 172, 181 can be used as magnetic position sensors as described in greater detail in relation to FIG. 1. The magnetic sensor circuit can include a first loop circuit 180 including the first loop 181 and proximal trace conductors 182 configured to deliver electrical signals sensed by the first loop 181 to the PIU 30 (FIG. 1). The magnetic sensor circuit can include a second loop circuit 170 including the second loop 171, the third loop 172, and proximal trace conductors 173 configured to deliver electrical signals sensed by the second and third loops 171, 172 to the PIU 30. The magnetic sensor circuit may be included in a patterned conductor layer of a flex circuit of the first membrane 110 and/or the second membrane 120.

Having shown and described exemplary embodiments of the subject matter contained herein, further adaptations of the methods and systems described herein may be accomplished by appropriate modifications without departing from the scope of the claims. For instance, catheters disclosed in references incorporated herein by reference and/or attached in the Appendix of priority Patent Application No. 63/507,154m can be modified to include one or more electrode combinations 130 or arrangements thereof as disclosed herein as understood by a person skilled in the pertinent art. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings. The following clauses list non-limiting embodiments of the disclosure:

Clause 1. An end effector for a medical probe comprising: a first electrode on a first side of the end effector, the first electrode comprising a first surface exposed to ambient environment and configured to contact tissue; and a second electrode on the first side of the end effector, the second electrode being at least partially circumscribed by the first electrode, the second electrode comprising a second surface exposed to the ambient environment and inhibited from contacting tissue by virtue of a first vertical gap between the first surface and the second surface.

Clause 2. An end effector for a medical probe comprising: a frame member that extends along a longitudinal axis; and first and second electrodes disposed generally orthogonal with respect to the longitudinal axis of the frame member so that one of the first and second electrodes is recessed with respect to the other of the first and second electrodes to prevent such recessed electrode from tissue contact.

Clause 3. The end effector of clause 2, wherein the first and second electrodes are disposed on a substrate spaced apart and not in contact with the frame member.

Clause 4. The end effector of clause 3 wherein the frame member is encapsulated in a polymer to maintain a gap from the frame member to the first and second electrodes.

Clause 5. The end effector of any one of clauses 1-4, wherein the second electrode is entirely circumscribed by the first electrode.

Clause 6. The end effector of any one of clauses 1-4, wherein the first electrode comprises a plurality of arcuate sections disposed around a perimeter of the second electrode such that plurality of arcuate sections are spaced apart from each other.

Clause 7. The end effector of any one of clauses 1-6, the first electrode comprising one of an annular shape or a segmented annulus, and the second electrode comprising one of a circular shape or a polygon.

Clause 8. The end effector of clause 7, the first electrode comprising a first outer diameter measuring from about 0.5 mm to about 0.67 mm.

Clause 9. The end effector of clause 7 or 8, the second electrode comprising a second outer diameter measuring about 0.44 mm.

Clause 10. The end effector of any one of clauses 1-9, the first electrode comprising a first surface area generally equal to a second surface area of the second electrode.

Clause 11. The end effector of any one of clauses 1-10, the first electrode comprising a first surface area measuring about 0.15 $mm^2$.

Clause 12. The end effector of any one of clauses 1-10, the second electrode comprising a second surface area measuring about 0.15 $mm^2$.

Clause 13. The end effector of any one of clauses 1-12, the first surface being spaced laterally from the second surface by a first lateral gap area having approximately equal surface area as the first surface area and/or the second surface area, and the first lateral gap area being a planar surface area parallel to the first surface, parallel to the second surface, and between the first surface and the second surface.

Clause 14. The end effector of any one of clauses 1-13, the first surface being spaced laterally from the second surface by a first lateral gap area that is approximately equal or less than the first surface area and that is approximately equal or less than the second surface area, the first lateral gap area being a planar surface area parallel to the first surface, parallel to the second surface, and between the first surface and the second surface, the first surface comprising an annular width equal to or greater than an annular width of the first lateral gap area, and the second surface comprising a diameter equal to or greater than the annular width of the first lateral gap area.

Clause 15. The end effector of clause 14, wherein the annular width of the first lateral gap area is approximately equal to 0.83 times the second surface area and/or 0.83 times the first surface area.

Clause 16. The end effector of any one of clauses 1-15, the first electrode being configured to measure electrocardiogram signals from tissue, and the second electrode being configured to sense far-field signals.

Clause 17. The end effector of any one of clauses 1-16, the first surface and the second surface comprising planar surfaces.

Clause 18. The end effector of any one of clauses 1-17, the first surface and the second surface extending along a longitudinal axis and facing orthogonal to the longitudinal axis.

Clause 19. The end effector of any one of clauses 1-18, further comprising: a first side comprising a depression such that the first electrode is coupled to the first side and circumscribing the depression and the second electrode is disposed in the depression.

Clause 20. The end effector of clause 19, wherein the second electrode is coupled to the first side at a bottom of the depression, and the depression comprises a larger diameter at the bottom compared to a diameter at a top of the depression.

Clause 21. The end effector of any one of clauses 1-20, further comprising: a third electrode coupled to a first side of the end effector and comprising a third surface exposed to ambient environment and configured to contact tissue, the third surface being coplanar with the first surface, and the third surface being spaced apart from the first surface by a second lateral gap; and a fourth electrode coupled to the first side of the end effector and circumscribed by the third electrode, the fourth electrode comprising a fourth surface exposed to the ambient environment and inhibited from contacting tissue by virtue of a second vertical gap between the third surface and the fourth surface such that the second vertical gap is measured substantially orthogonal to the third surface and orthogonal to the fourth surface.

Clause 22. The end effector of clause 21, the first electrode and the third electrode being configured to measure electrocardiogram signals as a bipolar pair.

Clause 23. The end effector of clause 21 or 22, the second surface being laterally spaced from the fourth surface by about 0.85 mm as measured from a central point of the second surface to a central point of the fourth surface.

Clause 24. The end effector of any one of clauses 21-23, the first electrode being longitudinally aligned with the third electrode and second electrode being longitudinally aligned with the fourth electrode.

Clause 25. The end effector of any one of clauses 21-24, further comprising: a plurality of bipolar pairs, each of the bipolar pairs comprising a first electrode combination and a second electrode combination, the first electrode combination comprising the first electrode and the second electrode, the second electrode combination comprising a third electrode circumscribing a fourth electrode that is vertically depressed in relation to the third electrode.

Clause 26. The end effector of clause 25, the plurality of bipolar pairs comprising a second bipolar pair spaced apart from a first bipolar pair by about 2.4 mm as measured from a central point or center of mass of surface areas of the first bipolar pair and a central point or center of mass of surface areas of the second bipolar pair.

Clause 27. The end effector of clause 25 or 26, the plurality of bipolar pairs comprising between six and twenty-four bipolar pairs.

Clause 28. The end effector of any one of clauses 1-27, further comprising: a fifth electrode coupled to a second side of the end effector facing in an opposite direction of the first side, the fifth electrode comprising a fifth surface exposed to ambient environment, and the fifth surface being aligned vertically with the first surface of the first electrode; and a sixth electrode coupled to the second side and circumscribed by the fifth electrode, the sixth electrode comprising a sixth surface exposed to the ambient environment and spaced with a third vertical gap between the fifth surface and the sixth surface such that the third vertical gap is measured orthogonal to the fifth surface and orthogonal to the sixth surface.

Clause 29. The end effector of clause 28, the fifth electrode being configured as a reference electrode to the first electrode.

Clause 30. The end effector of any one of clauses 1-29, the end effector being substantially planar along a longitudinal axis.

Clause 31. The end effector of any one of clauses 1-30, further comprising: a frame comprising one or more struts extending along a longitudinal axis; and a first membrane extending between the one or more struts on a first side of the end effector and being exposed to ambient environment, the first electrode and the second electrode being affixed to the first membrane such that the second electrode is disposed within a recess of the first membrane.

Clause 32. The end effector of clause 31, further comprising: a plurality of first electrode combinations affixed to the first membrane and forming rows and columns of an electrode array such that each electrode combination of the plurality of first electrode combinations comprises a respective first electrode comprising a respective first surface exposed to ambient environment and configured to contact tissue a respective second electrode comprising a respective second surface exposed to the ambient environment and inhibited from contacting tissue by virtue of a respective first vertical gap between the respective first surface and the respective second surface such that the respective first vertical gap is measured orthogonal to the respective first surface and orthogonal to the respective second surface.

Clause 33. The end effector of clause 32, further comprising: a second membrane extending between the one or more struts such that at least a portion of the frame is between the first membrane and the second membrane, the second membrane being exposed to the ambient environment; and a plurality of second electrode combinations affixed to the second membrane so that each second electrode combination of the plurality of second electrode combinations is disposed substantially opposite a respective electrode combination of the plurality of first electrode combinations and spaced apart from each other, each electrode combination of the plurality of second electrode combinations comprises a respective first electrode comprising a respective first surface exposed to ambient environment and configured to contact tissue a respective second electrode comprising a respective second surface exposed to the ambient environment and inhibited from contacting tissue by virtue of a respective first vertical gap between the respective first surface and the respective second surface such that the respective first vertical gap is measured orthogonal to the respective first surface and orthogonal to the respective second surface.

Clause 34. The end effector of any one of clauses 1-33, wherein the end effector is configured to expand to a planar configuration, the end effector further comprising: a plurality of inductive loops coupled to the end effector such that each inductive loop of the plurality of inductive loops comprises a respective axis orthogonal to the end effector in the planar configuration.

Clause 35. The end effector of clause 34, wherein the plurality of inductive loops comprising a first inductive loop, a second inductive loop, and a third inductive loop, the first inductive loop being disposed approximate a distal end of the end effector, and wherein a majority of the second inductive loop and a majority of the third inductive loop are disposed in a proximal direction in relation to the first inductive loop.

Clause 36. The end effector of clause 35, wherein the second inductive loop is positioned in a mirror image of the third inductive loop.

Clause 37. A medical probe comprising: an elongated shaft extending along a longitudinal axis; an end effector coupled to a distal end of the elongated shaft; and a plurality of electrode combinations coupled to the end effector, each electrode combination of the plurality of electrode combinations comprising a respective inner electrode and a respective outer electrode disposed around at least a majority of the respective inner electrode and being vertically offset from the respective inner electrode, each respective inner electrode and each respective outer electrode being exposed to ambient environment.

Clause 38. The medical probe of clause 37, wherein each respective inner electrode being inhibited from contacting tissue by virtue of the respective outer electrode being vertically offset from the respective inner electrode.

Clause 39. The medical probe of clause 37 or 38, each respective first electrode being configured to measure electrocardiogram signals from tissue, and each respective second electrode being configured to sense far-field signals.

Clause 40. The medical probe of any one of clauses 37-39, the end effector comprising a bipolar pair comprising two electrode combinations of the plurality of electrode combinations such that the bipolar pair is configured to detect a voltage difference between the respective outer electrodes of the two electrode combinations of bipolar pair.

Clause 41. A method of reducing far-field signals acquired for intracardiac mapping, the method comprising: locating a first electrode and a second electrode on a generally planar member so that one of the first and second electrodes is recessed with respect to the other of the first and second electrodes; sensing far-field signals with the recessed one of the first and second electrodes; sensing cardiac signals with the other of the first and second electrodes; and subtracting far-field signals from the cardiac signals.

Clause 42. The method of clause 41, wherein the first electrode includes a first surface area, the second electrode includes a second surface area substantially equal to the first surface area.

Clause 43. The method of clause 41, wherein the first electrode at least partially circumscribes the second electrode.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

What is claimed is:

1. An end effector for a medical probe comprising:
- a frame member that extends along a longitudinal axis
- a first side of the end effector facing in an orthogonal direction relative to the longitudinal axis;
- at least one depression disposed on the first side;
- a plurality of electrodes comprising:
- first and second electrodes disposed on the first side substantially in the orthogonal direction with respect to the longitudinal axis of the frame member, the first electrode being planar and substantially circumscribing the second electrode, the second electrode being disposed in the at least one depression to prevent the second electrode from tissue contact.

2. The end effector of claim 1, wherein the first and second electrodes are disposed on a substrate spaced apart and not in contact with the frame member.

3. The end effector of claim 2 wherein the frame member is encapsulated in a polymer to maintain a gap from the frame member to the first and second electrodes.

4. The end effector of claim 1, wherein the second electrode is entirely circumscribed by the first electrode.

5. The end effector of claim 1, wherein the first electrode comprises a plurality of arcuate sections disposed around a perimeter of the second electrode such that plurality of arcuate sections are spaced apart from each other.

6. The end effector of claim 1, the first electrode comprising a first surface area generally equal to a second surface area of the second electrode.

7. The end effector of claim 1, the first electrode being configured to measure electrocardiogram signals from tissue, and the second electrode being configured to sense far-field signals.

8. The end effector of claim 1, further comprising:
- a plurality of bipolar pairs, each of the bipolar pairs comprising a first electrode combination and a second electrode combination, the first electrode combination comprising the first electrode and the second electrode, the second electrode combination comprising a third electrode circumscribing a fourth electrode that is vertically depressed in relation to the third electrode.

9. The end effector of claim 1, the end effector being substantially planar along a longitudinal axis.

10. The end effector of claim 1, further comprising:
- the frame member comprising one or more struts extending along a longitudinal axis; and
- a first membrane extending between the one or more struts on a first side of the end effector and being exposed to ambient environment, the first electrode and the second electrode being affixed to the first membrane such that the second electrode is disposed within a recess of the first membrane.

11. The end effector of claim 1, wherein the end effector is configured to expand to a planar configuration, the end effector further comprising:
- a plurality of inductive loops coupled to the end effector such that each inductive loop of the plurality of inductive loops comprises a respective axis orthogonal to the end effector in the planar configuration.

12. An end effector for a medical probe comprising:
- a first side of the end effector facing in an orthogonal direction relative to a longitudinal axis;
- a plurality of electrodes comprising:
  - a first electrode on the first side of the end effector, the first electrode being planar and comprising a first surface facing substantially in the orthogonal direction exposed to ambient environment and configured to contact tissue; and
  - a second electrode on the first side of the end effector, the second electrode being at least partially circumscribed by the first electrode, the second electrode comprising a second surface facing substantially in the orthogonal direction exposed to the ambient environment and inhibited from contacting tissue by virtue of a first vertical gap between the first surface and the second surface in the orthogonal direction.

13. The end effector of claim 12, the first surface and the second surface comprising planar surfaces.

14. The end effector of claim 12, the first surface and the second surface extending parallel to the longitudinal axis and facing orthogonal to the longitudinal axis.

15. The end effector of claim 12, further comprising:
- a frame member that extends along a longitudinal axis, wherein the first and second electrodes are disposed on a substrate spaced apart and not in contact with the frame member.

16. The end effector of claim 12, further comprising:
- a first side comprising a depression such that the first electrode is coupled to the first side and circumscribing the depression and the second electrode is disposed in the depression.

17. The end effector of claim 12, further comprising:

a third electrode coupled to a first side of the end effector and comprising a third surface exposed to ambient environment and configured to contact tissue, the third surface being coplanar with the first surface, and the third surface being spaced apart from the first surface by a second lateral gap; and a fourth electrode coupled to the first side of the end effector and circumscribed by the third electrode, the fourth electrode comprising a fourth surface exposed to the ambient environment and inhibited from contacting tissue by virtue of a second vertical gap between the third surface and the fourth surface such that the second vertical gap is measured substantially orthogonal to the third surface and orthogonal to the fourth surface.

18. The end effector of claim 17, the first electrode and the third electrode being configured to measure electrocardiogram signals as a bipolar pair.

19. The end effector of claim 12, further comprising:

a plurality of bipolar pairs, each of the bipolar pairs comprising a first electrode combination and a second electrode combination, the first electrode combination comprising the first electrode and the second electrode, the second electrode combination comprising a third electrode circumscribing a fourth electrode that is vertically depressed in relation to the third electrode.

* * * * *